(12) United States Patent
Weng et al.

(10) Patent No.: US 8,622,937 B2
(45) Date of Patent: *Jan. 7, 2014

(54) CONTROLLED HIGH EFFICIENCY LESION FORMATION USING HIGH INTENSITY ULTRASOUND

(75) Inventors: Lee Weng, Bellevue, WA (US); David M. Perozek, Mercer Island, WA (US); Jimin Zhang, Bellevue, WA (US)

(73) Assignee: Kona Medical, Inc., Menlo Park, CA (US)

( * ) Notice: Subject to any disclaimer, the term of this patent is extended or adjusted under 35 U.S.C. 154(b) by 728 days.

This patent is subject to a terminal disclaimer.

(21) Appl. No.: 12/247,969

(22) Filed: Oct. 8, 2008

(65) Prior Publication Data

US 2009/0036774 A1 Feb. 5, 2009

Related U.S. Application Data

(63) Continuation of application No. 10/633,726, filed on Aug. 4, 2003, now Pat. No. 7,470,241, which is a continuation of application No. 09/721,526, filed on Nov. 22, 2000, now Pat. No. 6,626,855.

(60) Provisional application No. 60/167,707, filed on Nov. 26, 1999.

(51) Int. Cl.
*A61H 23/00* (2006.01)
*A61B 8/00* (2006.01)

(52) U.S. Cl.
USPC .............................................. 601/2; 600/439

(58) Field of Classification Search
USPC ......................................... 601/2, 3; 600/439
See application file for complete search history.

(56) References Cited

U.S. PATENT DOCUMENTS 385,256 A 6/1888 Eggers
3,274,437 A 9/1966 Mastrup
(Continued)

FOREIGN PATENT DOCUMENTS

DE 4110308 10/1992
DE 4230415 3/1994
(Continued)

OTHER PUBLICATIONS

Takeuchi et al., Dec. 4, 1990, Relaxor ferroelectric transducers, IEEE Ultrasonics Symposium, pp. 697-705.
(Continued)

*Primary Examiner* — Long V. Le
*Assistant Examiner* — Katherine Fernandez
(74) *Attorney, Agent, or Firm* — Knobbe, Martens, Olson & Bear LLP

(57) ABSTRACT

An ultrasound system used for both imaging and delivery high intensity ultrasound energy therapy to treatment sites and a method for treating tumors and other undesired tissue within a patient's body with an ultrasound device. The ultrasound device has an ultrasound transducer array disposed on a distal end of an elongate, relatively thin shaft. In one form of the invention, the transducer array is disposed within a liquid-filled elastomeric material that more effectively couples ultrasound energy into the tumor, that is directly contacted with the device. Using the device in a continuous wave mode, a necrotic zone of tissue having a desired size and shape (e.g., a necrotic volume selected to interrupt a blood supply to a tumor) can be created by controlling at least one of the f-number, duration, intensity, and direction of the ultrasound energy administered. This method speeds the therapy and avoids continuously pausing to enable intervening normal tissue to cool.

12 Claims, 10 Drawing Sheets

(56) References Cited

U.S. PATENT DOCUMENTS

| | | |
|---|---|---|
| 3,499,437 A | 3/1970 | Balamuth |
| 3,552,382 A | 1/1971 | Mount |
| 3,847,016 A | 11/1974 | Ziedonis |
| 3,927,662 A | 12/1975 | Ziedonis |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pedersen |
| 4,237,901 A | 12/1980 | Taenzer |
| 4,273,127 A | 6/1981 | Auth et al. |
| 4,315,514 A | 2/1982 | Drewes et al. |
| 4,469,099 A | 9/1984 | McEwen |
| 4,479,494 A | 10/1984 | McEwen |
| 4,484,569 A | 11/1984 | Driller et al. |
| 4,545,386 A | 10/1985 | Hetz et al. |
| 4,594,895 A | 6/1986 | Fujii |
| 4,601,296 A | 7/1986 | Yerushalmi |
| 4,605,010 A | 8/1986 | McEwen |
| 4,688,578 A | 8/1987 | Takano et al. |
| 4,708,836 A | 11/1987 | Gain et al. |
| 4,748,985 A | 6/1988 | Nagasaki |
| 4,757,820 A | 7/1988 | Itoh |
| 4,770,175 A | 9/1988 | McEwen |
| 4,773,865 A | 9/1988 | Baldwin |
| 4,784,148 A | 11/1988 | Dow et al. |
| 4,841,979 A * | 6/1989 | Dow et al. ............ 600/446 |
| 4,850,363 A | 7/1989 | Yanagawa |
| 4,858,613 A | 8/1989 | Fry et al. |
| 4,905,672 A | 3/1990 | Schwarze et al. |
| 4,913,155 A | 4/1990 | Dow et al. |
| 4,929,246 A | 5/1990 | Sinofsky |
| 4,931,047 A | 6/1990 | Broadwin et al. |
| 4,938,216 A | 7/1990 | Lele |
| 4,938,217 A | 7/1990 | Lele |
| 4,957,099 A | 9/1990 | Hassler |
| 5,005,579 A | 4/1991 | Wurster et al. |
| RE33,590 E | 5/1991 | Dory |
| 5,026,387 A | 6/1991 | Thomas |
| 5,036,855 A | 8/1991 | Fry et al. |
| 5,039,774 A | 8/1991 | Shikinami et al. |
| 5,042,486 A | 8/1991 | Pfeiler et al. |
| 5,065,742 A | 11/1991 | Belikan et al. |
| 5,080,101 A | 1/1992 | Dory |
| 5,080,102 A | 1/1992 | Dory |
| 5,150,712 A | 9/1992 | Dory |
| 5,170,790 A | 12/1992 | Lacoste et al. |
| 5,178,135 A | 1/1993 | Uchiyama et al. |
| 5,178,148 A | 1/1993 | Lacoste et al. |
| 5,181,522 A | 1/1993 | McEwen |
| 5,194,291 A | 3/1993 | D'Aoust et al. |
| 5,211,160 A | 5/1993 | Talish et al. |
| 5,215,680 A | 6/1993 | D'Arrigo |
| 5,219,401 A | 6/1993 | Cathignol et al. |
| 5,230,334 A | 7/1993 | Klopotek |
| 5,230,921 A | 7/1993 | Waltonen et al. |
| 5,233,994 A | 8/1993 | Shmulewitz |
| 5,243,988 A | 9/1993 | Sieben et al. |
| 5,254,087 A | 10/1993 | McEwen |
| 5,263,957 A | 11/1993 | Davison |
| 5,290,278 A | 3/1994 | Anderson |
| 5,307,816 A | 5/1994 | Hashimoto et al. |
| 5,311,869 A | 5/1994 | Okazaki |
| 5,312,431 A | 5/1994 | McEwen |
| 5,318,035 A | 6/1994 | Konno et al. |
| 5,352,195 A | 10/1994 | McEwen |
| 5,364,389 A | 11/1994 | Anderson |
| 5,383,896 A | 1/1995 | Gershony et al. |
| 5,391,140 A | 2/1995 | Schaetzle et al. |
| 5,391,197 A | 2/1995 | Burdette et al. |
| 5,394,877 A | 3/1995 | Orr et al. |
| 5,415,657 A | 5/1995 | Taymor-Luria |
| 5,439,477 A | 8/1995 | McEwen |
| 5,453,576 A | 9/1995 | Krivitski |
| 5,454,373 A | 10/1995 | Koger et al. |
| 5,454,831 A | 10/1995 | McEwen |
| 5,471,988 A | 12/1995 | Fujio et al. |
| 5,474,071 A | 12/1995 | Chapelon et al. |
| 5,492,126 A | 2/1996 | Hennige et al. |
| 5,503,152 A | 4/1996 | Oakley et al. |
| 5,507,744 A | 4/1996 | Tay et al. |
| 5,507,790 A | 4/1996 | Weiss |
| 5,515,853 A | 5/1996 | Smith et al. |
| 5,520,188 A | 5/1996 | Hennige et al. |
| 5,522,878 A | 6/1996 | Montecalvo et al. |
| 5,524,620 A | 6/1996 | Rosenschein |
| 5,526,815 A | 6/1996 | Granz et al. |
| 5,534,232 A | 7/1996 | Denes et al. |
| 5,536,489 A | 7/1996 | Lohrmann et al. |
| 5,553,618 A | 9/1996 | Suzuki et al. |
| 5,556,415 A | 9/1996 | McEwen et al. |
| 5,558,092 A | 9/1996 | Unger et al. |
| 5,573,497 A | 11/1996 | Chapelon |
| 5,578,055 A | 11/1996 | McEwen |
| 5,584,853 A | 12/1996 | McEwen |
| 5,590,657 A | 1/1997 | Cain et al. |
| 5,601,526 A | 2/1997 | Chapelon et al. |
| 5,607,447 A | 3/1997 | McEwen et al. |
| 5,609,485 A | 3/1997 | Bergman et al. |
| 5,626,601 A | 5/1997 | Gershony et al. |
| 5,628,730 A | 5/1997 | Shapland et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,655,539 A | 8/1997 | Wang et al. |
| 5,657,760 A | 8/1997 | Ying et al. |
| 5,665,073 A | 9/1997 | Bulow et al. |
| 5,666,954 A * | 9/1997 | Chapelon et al. ............ 600/439 |
| 5,681,339 A | 10/1997 | McEwen et al. |
| 5,685,307 A | 11/1997 | Holland et al. |
| 5,695,493 A | 12/1997 | Nakajima et al. |
| 5,697,897 A | 12/1997 | Buchholtz et al. |
| D389,574 S | 1/1998 | Emerson et al. |
| 5,704,361 A | 1/1998 | Seward et al. |
| 5,711,058 A | 1/1998 | Frey et al. |
| 5,713,363 A | 2/1998 | Seward et al. |
| 5,716,374 A | 2/1998 | Francese et al. |
| 5,720,286 A | 2/1998 | Chapelon et al. |
| 5,720,287 A | 2/1998 | Chapelon et al. |
| 5,726,066 A | 3/1998 | Choi |
| 5,735,796 A | 4/1998 | Granz et al. |
| 5,738,635 A | 4/1998 | Chapelon et al. |
| 5,741,295 A | 4/1998 | McEwen |
| 5,755,228 A | 5/1998 | Wilson et al. |
| 5,762,066 A * | 6/1998 | Law et al. ............ 600/439 |
| 5,769,790 A | 6/1998 | Watkins et al. |
| 5,788,636 A | 8/1998 | Curley |
| 5,807,285 A | 9/1998 | Vaitekunas et al. |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,879,314 A | 3/1999 | Peterson et al. |
| 5,882,302 A | 3/1999 | Driscoll, Jr. et al. |
| 5,895,356 A * | 4/1999 | Andrus et al. ............ 600/439 |
| 5,904,659 A * | 5/1999 | Duarte et al. ............ 601/2 |
| 5,906,580 A | 5/1999 | Kline-Schoder et al. |
| 5,911,735 A | 6/1999 | McEwen |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |

(56) References Cited

U.S. PATENT DOCUMENTS

| | | |
|---|---|---|
| 5,931,853 A | 8/1999 | McEwen |
| 5,935,144 A | 8/1999 | Estabrook |
| 5,935,146 A | 8/1999 | McEwen |
| 5,935,339 A | 8/1999 | Henderson et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A | 12/1999 | Martin et al. |
| 6,013,031 A | 1/2000 | Mendlein et al. |
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |
| 6,039,694 A | 3/2000 | Larson et al. |
| 6,042,556 A | 3/2000 | Beach et al. |
| 6,050,943 A | 4/2000 | Slayton et al. |
| 6,067,371 A | 5/2000 | Gouge et al. |
| 6,068,596 A | 5/2000 | Weth et al. |
| 6,071,239 A | 6/2000 | Cribbs et al. |
| 6,071,277 A | 6/2000 | Farley et al. |
| 6,078,831 A | 6/2000 | Belef et al. |
| 6,083,159 A | 7/2000 | Driscoll, Jr. et al. |
| 6,087,761 A | 7/2000 | Lorraine et al. |
| 6,102,860 A | 8/2000 | Mooney |
| 6,106,463 A | 8/2000 | Wilk |
| 6,120,453 A | 9/2000 | Sharp |
| 6,128,522 A | 10/2000 | Acker et al. |
| 6,179,831 B1 | 1/2001 | Bliweis |
| 6,182,341 B1 | 2/2001 | Talbot et al. |
| 6,200,539 B1 | 3/2001 | Sherman et al. |
| 6,206,843 B1 | 3/2001 | Iger et al. |
| 6,213,939 B1 | 4/2001 | McEwen |
| 6,217,530 B1 | 4/2001 | Martin et al. |
| 6,221,015 B1 | 4/2001 | Yock |
| 6,231,507 B1 | 5/2001 | Zikorus et al. |
| 6,233,477 B1 | 5/2001 | Chia et al. |
| 6,246,156 B1 | 6/2001 | Takeuchi et al. |
| 6,254,601 B1 | 7/2001 | Burbank et al. |
| 6,259,945 B1 | 7/2001 | Epstein et al. |
| 6,261,233 B1 | 7/2001 | Kantorovich |
| 6,263,551 B1 | 7/2001 | Lorraine et al. |
| 6,267,734 B1 | 7/2001 | Ishibashi et al. |
| 6,270,458 B1 | 8/2001 | Barnea |
| 6,277,077 B1 | 8/2001 | Brisken et al. |
| 6,311,692 B1 | 11/2001 | Vaska et al. |
| 6,315,441 B2 | 11/2001 | King |
| 6,332,089 B1 | 12/2001 | Acker et al. |
| 6,361,496 B1 | 3/2002 | Zikorus et al. |
| 6,361,548 B1 | 3/2002 | McEwen |
| 6,399,149 B1 | 6/2002 | Klett et al. |
| 6,406,759 B1 | 6/2002 | Roth |
| 6,409,720 B1 | 6/2002 | Hissong et al. |
| 6,419,669 B1 | 7/2002 | Frazier et al. |
| 6,425,867 B1 | 7/2002 | Vaezy et al. |
| 6,425,876 B1 | 7/2002 | Frangi et al. |
| 6,432,067 B1 | 8/2002 | Martin et al. |
| 6,443,894 B1 | 9/2002 | Sumanaweera et al. |
| 6,453,526 B2 | 9/2002 | Lorraine et al. |
| 6,488,639 B1 | 12/2002 | Ribault et al. |
| 6,491,672 B2 | 12/2002 | Slepian et al. |
| 6,494,848 B1 | 12/2002 | Sommercorn et al. |
| 6,500,133 B2 | 12/2002 | Martin et al. |
| 6,520,915 B1 | 2/2003 | Lin et al. |
| 6,522,926 B1 | 2/2003 | Kieval et al. |
| 6,548,047 B1 | 4/2003 | Unger |
| 6,551,576 B1 | 4/2003 | Unger et al. |
| 6,559,644 B2 | 5/2003 | Froundlich et al. |
| 6,562,037 B2 | 5/2003 | Paton et al. |
| 6,565,557 B1 | 5/2003 | Sporri et al. |
| 6,576,168 B2 | 6/2003 | Hardcastle et al. |
| 6,584,360 B2 | 6/2003 | Francischelli et al. |
| 6,595,934 B1 | 7/2003 | Hissong et al. |
| 6,599,256 B1 | 7/2003 | Acker et al. |
| 6,599,288 B2 | 7/2003 | Maguire et al. |
| 6,602,251 B2 | 8/2003 | Burbank et al. |
| 6,612,988 B2 | 9/2003 | Maor et al. |
| 6,616,624 B1 | 9/2003 | Kieval |
| 6,626,855 B1 | 9/2003 | Weng et al. |
| 6,633,658 B1 | 10/2003 | Dabney et al. |
| 6,652,461 B1 | 11/2003 | Levkovitz |
| 6,656,131 B2 | 12/2003 | Alster et al. |
| 6,656,136 B1 | 12/2003 | Weng et al. |
| 6,676,601 B1 | 1/2004 | Lacoste et al. |
| 6,682,483 B1 | 1/2004 | Abend et al. |
| 6,685,639 B1 | 2/2004 | Wang et al. |
| 6,706,892 B1 | 3/2004 | Ezrin et al. |
| 6,709,392 B1 | 3/2004 | Salgo et al. |
| 6,709,407 B2 | 3/2004 | Fatemi |
| 6,716,184 B2 | 4/2004 | Vaezy et al. |
| 6,719,694 B2 | 4/2004 | Weng et al. |
| 6,719,699 B2 | 4/2004 | Smith |
| 6,726,627 B1 | 4/2004 | Lizzi et al. |
| 6,735,461 B2 | 5/2004 | Vitek et al. |
| 6,755,789 B2 | 6/2004 | Stringer et al. |
| 6,764,488 B1 | 7/2004 | Burbank et al. |
| 6,846,291 B2 | 1/2005 | Smith et al. |
| 6,868,739 B1 | 3/2005 | Krivitski et al. |
| 6,875,176 B2 | 4/2005 | Mourad et al. |
| 6,875,420 B1 | 4/2005 | Quay |
| 6,905,498 B2 | 6/2005 | Hooven |
| 6,932,771 B2 | 8/2005 | Whitmore et al. |
| 6,955,648 B2 | 10/2005 | Mozayeni et al. |
| 6,978,174 B2 | 12/2005 | Gelfand et al. |
| 7,022,077 B2 | 4/2006 | Mourad et al. |
| 7,052,463 B2 | 5/2006 | Peszynski et al. |
| 7,063,666 B2 | 6/2006 | Weng et al. |
| 7,128,711 B2 | 10/2006 | Medan et al. |
| 7,149,564 B2 | 12/2006 | Vining et al. |
| 7,162,303 B2 | 1/2007 | Levin et al. |
| 7,211,060 B1 | 5/2007 | Talish et |
| 7,260,250 B2 | 8/2007 | Summers et al. |
| 7,285,093 B2 | 10/2007 | Anisimov et al. |
| 7,445,599 B2 | 11/2008 | Kelly et al. |
| 7,470,241 B2 | 12/2008 | Weng et al. |
| 7,499,748 B2 | 3/2009 | Moffitt et al. |
| 7,510,536 B2 | 3/2009 | Foley et al. |
| 7,530,958 B2 | 5/2009 | Slayton et al. |
| 7,534,209 B2 | 5/2009 | Abend et al. |
| 7,553,284 B2 | 6/2009 | Vaitekunas |
| 7,617,005 B2 | 11/2009 | Demarais et al. |
| 7,620,451 B2 | 11/2009 | Demarais et al. |
| 7,628,764 B2 | 12/2009 | Duarte et al. |
| 7,684,865 B2 | 3/2010 | Aldrich et al. |
| 7,697,972 B2 | 4/2010 | Verard et al. |
| 2001/0014775 A1 | 8/2001 | Koger et al. |
| 2001/0014805 A1 | 8/2001 | Burbank et al. |
| 2001/0032382 A1 | 10/2001 | Lorraine et al. |
| 2001/0041910 A1 | 11/2001 | McEwen |
| 2001/0044636 A1 | 11/2001 | Pedros et al. |
| 2002/0032394 A1 | 3/2002 | Brisken et al. |
| 2002/0055736 A1 | 5/2002 | Horn et al. |
| 2002/0095164 A1 | 7/2002 | Andreas et al. |
| 2002/0193831 A1 | 12/2002 | Smith, III |
| 2003/0009194 A1 | 1/2003 | Saker et al. |
| 2003/0018255 A1 | 1/2003 | Martin et al. |
| 2003/0036771 A1 | 2/2003 | McEwen et al. |
| 2003/0050665 A1 | 3/2003 | Ginn |
| 2003/0069569 A1 | 4/2003 | Burdette et al. |
| 2003/0114756 A1 | 6/2003 | Li |
| 2003/0120204 A1 | 6/2003 | Unger et al. |
| 2003/0153849 A1 | 8/2003 | Huckle et al. |
| 2003/0195420 A1 | 10/2003 | Mendlein et al. |
| 2003/0208101 A1 | 11/2003 | Cecchi |
| 2003/0216792 A1 | 11/2003 | Levin et al. |
| 2004/0002654 A1 | 1/2004 | Davidson et al. |
| 2004/0030227 A1 | 2/2004 | Littrup et al. |
| 2004/0030268 A1 | 2/2004 | Weng et al. |
| 2004/0054287 A1 | 3/2004 | Stephens |
| 2004/0054289 A1 | 3/2004 | Eberle et al. |
| 2004/0078034 A1 | 4/2004 | Acker et al. |

(56) References Cited

U.S. PATENT DOCUMENTS

| | | |
|---|---|---|
| 2004/0078219 A1 | 4/2004 | Kaylor |
| 2004/0082978 A1 | 4/2004 | Harrison et al. |
| 2004/0097840 A1 | 5/2004 | Holmer |
| 2004/0106880 A1 | 6/2004 | Weng et al. |
| 2004/0113524 A1 | 6/2004 | Baumgartner et al. |
| 2004/0122493 A1 | 6/2004 | Ishibashi et al. |
| 2004/0127798 A1 | 7/2004 | Dala-Krishna et al. |
| 2004/0153126 A1 | 8/2004 | Okai |
| 2004/0158154 A1 | 8/2004 | Hanafy et al. |
| 2004/0234453 A1 | 11/2004 | Smith |
| 2004/0254620 A1 | 12/2004 | Lacoste et al. |
| 2004/0267252 A1 | 12/2004 | Washington et al. |
| 2005/0043625 A1 | 2/2005 | Oliver et al. |
| 2005/0046311 A1 | 3/2005 | Baumgartner et al. |
| 2005/0054955 A1 | 3/2005 | Lidgren |
| 2005/0065436 A1 | 3/2005 | Ho et al. |
| 2005/0070790 A1 | 3/2005 | Niwa et al. |
| 2005/0085793 A1 | 4/2005 | Glossop |
| 2005/0090104 A1 | 4/2005 | Yang et al. |
| 2005/0096542 A1 | 5/2005 | Weng et al. |
| 2005/0124884 A1 | 6/2005 | Bolorforosh et al. |
| 2005/0154299 A1 | 7/2005 | Hoctor et al. |
| 2005/0165298 A1 | 7/2005 | Larson et al. |
| 2005/0182297 A1 | 8/2005 | Gravenstein et al. |
| 2005/0182319 A1 | 8/2005 | Glossop |
| 2005/0240102 A1 | 10/2005 | Rachlin et al. |
| 2005/0240103 A1 | 10/2005 | Byrd et al. |
| 2005/0240126 A1 | 10/2005 | Foley et al. |
| 2005/0240170 A1 | 10/2005 | Zhang et al. |
| 2006/0025756 A1 | 2/2006 | Francischelli et al. |
| 2006/0058678 A1 | 3/2006 | Vitek et al. |
| 2006/0122514 A1 | 6/2006 | Byrd et al. |
| 2006/0184069 A1 | 8/2006 | Vaitekunas |
| 2006/0235300 A1 | 10/2006 | Weng et al. |
| 2007/0004984 A1 | 1/2007 | Crum et al. |
| 2007/0055155 A1 | 3/2007 | Owen et al. |
| 2007/0106339 A1 | 5/2007 | Errico et al. |
| 2007/0129720 A1 | 6/2007 | Demarais et al. |
| 2007/0142879 A1 | 6/2007 | Greenberg et al. |
| 2007/0149880 A1 | 6/2007 | Willis |
| 2007/0167806 A1 | 7/2007 | Wood et al. |
| 2007/0179379 A1 | 8/2007 | Weng et al. |
| 2007/0213616 A1 | 9/2007 | Anderson et al. |
| 2007/0233185 A1 | 10/2007 | Anderson et al. |
| 2007/0239000 A1 | 10/2007 | Emery et al. |
| 2007/0265687 A1 | 11/2007 | Deem et al. |
| 2008/0033292 A1 | 2/2008 | Shafran |
| 2008/0039746 A1 | 2/2008 | Hissong et al. |
| 2008/0045864 A1 | 2/2008 | Candy et al. |
| 2008/0045865 A1 | 2/2008 | Kislev |
| 2008/0047325 A1 | 2/2008 | Bartlett |
| 2008/0200815 A1 | 8/2008 | Van Der Steen et al. |
| 2008/0234569 A1 | 9/2008 | Tidhar et al. |
| 2008/0255498 A1 | 10/2008 | Houle |
| 2008/0255642 A1 | 10/2008 | Zarins et al. |
| 2008/0312561 A1 | 12/2008 | Chauhan |
| 2008/0317204 A1 | 12/2008 | Sumanaweera et al. |
| 2008/0319375 A1 | 12/2008 | Hardy |
| 2009/0012098 A1 | 1/2009 | Jordan et al. |
| 2009/0036948 A1 | 2/2009 | Levin et al. |
| 2009/0054770 A1 | 2/2009 | Daigle |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0088623 A1 | 4/2009 | Vortman et al. |
| 2009/0112095 A1 | 4/2009 | Daigle |
| 2009/0112133 A1 | 4/2009 | Deisseroth et al. |
| 2009/0163982 A1 | 6/2009 | deCharms |
| 2009/0221939 A1 | 9/2009 | Demarais et al. |
| 2009/0247911 A1 | 10/2009 | Novak et al. |
| 2009/0264755 A1 | 10/2009 | Chen et al. |
| 2009/0306644 A1 | 12/2009 | Mayse et al. |
| 2009/0326379 A1 | 12/2009 | Daigle et al. |
| 2010/0092424 A1 | 4/2010 | Sanghvi et al. |
| 2010/0125269 A1 | 5/2010 | Emmons et al. |
| 2010/0174188 A1 | 7/2010 | Wang et al. |
| 2011/0028867 A1 | 2/2011 | Choo et al. |
| 2011/0118602 A1 | 5/2011 | Weng et al. |
| 2011/0178403 A1 | 7/2011 | Weng et al. |
| 2011/0178445 A1 | 7/2011 | Weng et al. |
| 2011/0230763 A1 | 9/2011 | Emery et al. |
| 2011/0230796 A1 | 9/2011 | Emery et al. |

FOREIGN PATENT DOCUMENTS

| | | |
|---|---|---|
| DE | 102 09 380 | 9/2003 |
| EP | 0 225 120 | 6/1987 |
| EP | 0 239 999 | 10/1987 |
| EP | 0 383 270 | 8/1990 |
| EP | 0420758 | 4/1991 |
| EP | 0 679 371 | 11/1995 |
| EP | 1 219 245 | 7/2002 |
| EP | 1265223 | 12/2002 |
| EP | 1 449 563 | 8/2004 |
| EP | 1874192 A1 | 10/2006 |
| EP | 2181342 A1 | 2/2009 |
| EP | 2303131 | 12/2009 |
| FR | 2672486 | 8/1992 |
| WO | WO 9731364 | 8/1997 |
| WO | WO 98/11840 | 3/1998 |
| WO | WO 98/58588 | 12/1998 |
| WO | WO 99/07432 | 2/1999 |
| WO | WO 99/22652 | 5/1999 |
| WO | WO 99/048621 | 9/1999 |
| WO | WO 0072919 | 12/2000 |
| WO | WO 01/34018 | 5/2001 |
| WO | WO 02069805 | 9/2002 |
| WO | WO 2004/064598 | 8/2004 |
| WO | WO 2004/086086 | 10/2004 |
| WO | WO 2005/030295 | 4/2005 |
| WO | WO 2005/056105 | 6/2005 |
| WO | WO 2006/113445 | 10/2006 |
| WO | WO 2007/073551 | 6/2007 |
| WO | WO 2009/018394 | 2/2009 |
| WO | WO 2009/026534 | 2/2009 |
| WO | WO 2009/158399 | 12/2009 |
| WO | WO 2011/053757 | 5/2011 |
| WO | WO 2011/053772 | 5/2011 |

OTHER PUBLICATIONS

Office Action dated Dec. 8, 2011 for U.S. Appl. No. 11/955,310.
Office Action dated Feb. 3, 2012 for U.S. Appl. No. 13/245,689.
Final Office Action dated Jun. 13, 2012 for U.S. Appl. No. 13/245,689.
Office Action dated Jun. 7, 2012 for U.S. Appl. No. 13/344,418.
Office Action dated Jun. 11, 2012 for U.S. Appl. No. 13/346,466.
Office Action dated Dec. 30, 2011 for U.S. Appl. No. 12/896,740.
Final Office Action dated Jun. 5, 2012 for U.S. Appl. No. 12/896,740.
Office Action dated Oct. 25, 2011 for U.S. Appl. No. 13/025,959.
Office Action dated Dec. 15, 2011 for U.S. Appl. No. 13/026108.
Final Office Action dated May 14, 2012 for U.S. Appl. No. 12/026108.
Office Action dated Nov. 30, 2011 for U.S. Appl. No. 13/011,533.
Final Office Action dated May 2, 2012 for U.S. Appl. No. 13/011,533.
Advisory Action dated Jul. 16, 2012 for U.S. Appl. No. 13/011,533.
Office Action dated Jul. 10, 2012 for U.S. Appl. No. 12/951,850.
Final Office Action dated May 10, 2012 for U.S. Appl. No. 11/583,656.
Office Action dated May 24, 2012 for U.S. Appl. No. 13/118,144.
First Action Interview Office Action Summary dated May 30, 2012 for U.S. Appl. No. 13/245,703.
Office Action dated Apr. 6, 2012 for U.S. Appl. No. 12/685,655.
Office Action dated Apr. 10, 2012 for U.S. Appl. No. 12/725,450.
International Search Report and Written Opinion dated Jul. 27, 2011 for PCT Application No. PCT/US2011/033337.
International Search Report and Written Opinion dated Jun. 6, 2011 for PCT Application No. PCT/US2010/052197.
Office Action dated Mar. 20, 2012 for U.S. Appl. No. 13/246,775.
Office Action dated Nov. 28, 2011 for U.S. Appl. No. 13/246,763.

(56) References Cited

OTHER PUBLICATIONS

International Search Report and Written Opinion dated Dec. 6, 2010 for PCT Application No. PCT/US2010/052193.

Accord et al., "The Issue of Transmurality in Surgical Ablation for Atrial Fibrillation." Cardiothoracic Surgery Network: 3pp, Feb. 8, 2007.

Amenta et al., "A New Voronoi-Based Surface Reconstruction Algorithm." Computer Graphics: 7pp, 1998.

American Red Cross., "Blood 101." 4pp., Dec. 11, 2007.

Anand et al., "Monitoring formation of high intensity focused ultrasound (HIFU) induced lesions using backscattered ultrasound." Acoustical Society of America; Mar. 10, 2004.

Anand et al., "Using the ATL 1000 to Collect Domodulated RF Data for Monitoring HIFU Lesion Formation." Presented at SPIE Medical Imaging 2003. 11pp, 2003.

Aurenhammer, F. "Voronoi diagrams—A Survey of a Fundamental Geometric Data Structure." ACM Computing Surveys, vol. 23, No. 3: 345-405, Sep. 1991.

Bachmann et al., "Targeting Mucosal Addressin Cellular Adhesion Molecule (MAdCAM)-1 to Noninvasively Image Experimental Crohn's Disease." Gastroenterology; vol. 130: 8-16, 2006.

Barthe et al. "Efficient Wideband Linear Arrays for Imaging and Therapy" IEEE Ultrasonics Symposium. pp. 1249-1252 (1999).

Bauer et al., "Ultrasound Imaging with SonoVue: Low Mechanical Index Real-Time Imaging." Acad. Radiol.; vol. 9, Suppl. 2: S282-S284, 2002.

Beard et al., "An Annular Focus Ultrasonic Lens for Local Hyperthermia Treatment of Small Tumors." Ultrasound in Medicine & Biology; vol. 8, No. 2: 177-184, 1982.

Bokarewa et al., "Tissue factor as a proinflammatory agent." Arthritis Research, vol. 4: 190-195, Jan. 10, 2002.

Bots et al., "Intima Media Thickness as a Surrogate Marker for Generalised Atherosclerosis." Cardiovascular Drugs and Therapy, ProQuest Medical Library; vol. 16, No. 4: 341-351, Jul. 2002.

Brayman et al., "Erosion of Artificial Endothelia in Vitro by Pulsed Ultrasound: Acoustic Pressure, Frequency, Membrane Orientation and Microbubble Contrast Agent Dependence." Ultrasound in Medicine & Biology; vol. 25, No. 8: 1305-1320, 1999.

Buller et al., "Accurate Three-dimensional Wall Thickness Measurement From Multi-Slice Short-Axis MR Imaging." Computers in Cardiology, 245-248, 1995.

Byram et al., "3-D Phantom and in Vivo Cardiac Speckle Tracking Using a Matrix Array and Raw Echo Data." IEEE Transactions on Ultrasonics, Ferroelectrics, and Frequency Control, vol. 57, No. 4; 839-854, Apr. 2010.

Campese, V. Krol, E. Neurogenic Factors in Renal Hypertension. Current Hypertension Reports 2002, 4:256-260.

Canadian Examination Report dated Nov. 14, 2007 in CA Patent Application 2,387,127, filed Oct. 25, 2000.

Chao et al., "Aspheric lens design." Ultrasonics Symposium, 2000 IEEE, vol. 2: Abstract Only, Oct. 2000.

Chelule et al., "Fabrication of Medical Models From Scan Data via Rapid Prototyping Techniques." 9 pp., Feb. 7, 2007.

Chen et al., "A comparison of the fragmentation thresholds and inertial cavitation doses of different ultrasound contrast agents." Journal of the Acoustical Society of America, vol. 113, No. 1: 643-665, Jan. 2003.

Chen et al., "Inertial Cavitation Dose and Hemolysis Produced in Vitro With or Without Optison." Ultrasound in Medicine & Biology, vol. 29, No. 5: 725-737, 2003.

Chen et al., DC-Biased Electrostrictive Materials and Transducers for Medical Imaging, 1997 IEEE Ultrasonics Symposium, IEEE, Aug. 1997.

Chong et al., "Tissue Factor and Thrombin Mediate Myocardial Ischemia-Reperfusion Injury." The Society of Thoracic Surgeons, vol. 75: S649-655, 2003.

Damianou, et al., "Application of the Thermal Dose Concept for Predicting the Necrosed Tissue Volume. During Ultrasound Surgery", IEEE Ultrasonic Symposium, (1993) 1199-1202.

Dayton et al., "The magnitude of radiation force on ultrasound contrast agents." Journal of the Acoustical Society of America, vol. 112, No. 5, Part 1: 2183-2192, Nov. 2002.

Dempsey et al., "Thickness of Carotid Artery Atherosclerotic Plaque and Ischemic Risk." Neurosurgery, vol. 27, No. 3: 343-348, 1990.

Dewhirst, et al., "Basic principles of thermal dosimetry and thermal thresholds for tissue damage from hyperthermia", Int. J. Hyperthermia, (2003) 19(3):267-294,.

Dibona, G. F., et al., Chaotic behavior of renal sympathetic nerve activity: effect of baroreceptor denervation and cardiac failure, Am J Physiol Renal Physiol, 279:F491-501, 2000.

Dibona, G.F.: "Neural control of the kidney: functionally specific renal sympathetic nerve fibers." Am J. Physiol Regulatory Integrative Comp Physiol 279: R1517-1524, 2000.

Dibona, GF. Functionally Specific Renal Sympathetic Nerve Fibers: Role in Cardiovascular Regulation. American Journal of Hypertension. 2001 vol. 14(6) 163S-170S.

Doumas, M., et al., Renal Sympathetic Denervation: the Jury is Still Out, the Lancet, Nov. 2010, vol. 376, Issue 9756, pp. 1878-1880.

Ebbini et al., "Image-guided noninvasive surgery with ultrasound phased arrays." SPIE, vol. 3249: 230239, Apr. 2, 1998.

Edelsbrunner, Herbert. "Geometry and Topology for Mesh Generation." Cambridge University Press: 68pp, 2001.

Esler, Murray D., et al., Renal sympathetic denervation in patients with treatmentresistant hypertension (The Symplicity HTN-2 Trial): a randomised controlled trial, Nov. 2010, The Lancet, vol. 376, Issue 9756, pp. 1903-1909.

European Examination Report dated Mar. 7, 2008 in EP Patent Application 989717.4, filed Oct. 25, 2000.

Everbach et al., "Cavitational Mechanisms in Ultrasound-Accelerated Thrombolysis at 1 MHz." Ultrasound in Medicine & Biology, vol. 26, No. 7: 1153-1160, 2000.

Ewert et al., "Anti-myeloperoxidase antibodies stimulate neutrophils to damage human endothelial cells." Kidney International, vol. 41: 375-383, 1992.

Fjield et al.; "A parametric study of the concentric-ring transducer design for MRI guided ultrasound surgery." J. Acoust. Soc. Am 100 (2) Pt. 1, Aug. 1996.

Ganapathy et al., "A New General Triangulation Method for Planar Contours." Computer Graphics vol. 16, No. 3:69-75, 1982.

Grassi, G. Role of the Sympathetic Nervous System in Human Hypertension. Journal of Hypertension. 1998, 16: 1979-1987.

Gray, Henry. "The Skull." Anatomy of the Human Body: 7pp., 1918.

Guzman et al., "Ultrasound—Mediated Disruption of Cell Membranes. I. Quantification of Molecular uptake and Cell Viability. / II. Heterogeneous effects on cells." Journal of the Acoustical Society of America, vol. 110, No. 1: 588-606, Jul. 2001.

Hachimine, K. et. al. Sonodynamic Therapy of Cancer Using a Novel Porphyrin Derivative, DCPH-P-Na(I),which is Devoid of Photosensitivity. Cancer Science 2007; 98: 916-920.

Hadimioglu et al., "High-Efficiency Fresnel Acoustic Lenses." Ultrasonics Symposium 1993 IEEE: 579-582, 1993.

Han et al., "A Fast Minimal Path Active Contour Model." IEEE Transactions on Image Processing, vol. 10, No. 6: 865-873, Jun. 2001.

Hatangadi, Ram. "A Novel Dual Axis Multiplanar Transesophageal Ultrasound Probe for Three-Dimensional Echocardiograph." University of Washington, Department of Sciences and Engineering, vol. 55-11B: Abstract 1pg, 1994.

Holt et al., "Bubbles and Hifu: the Good, the Bad and the Ugly." Boston University, Department of Aerospace and Mechanical Engineering: 120-131, 2002.

Hubka et al., "Three-dimensional echocardiographic measurement of left ventricular wall thickness: in vitro and in vivo validation." Journal of the American Society of Echocardiography, vol. 15, No. 2: 129-135, 2002.

Hutchinson et al. "Intracavitary Ultrasound Phased Arrays for Noninvasive Prostate Surgery." IEEE Transactions on Ultrasonics. Ferroelectrics, and Frequency Control. 43(6):1032-1042 (1996).

Hwang et al., "Vascular Effects Induced by Combined 1-MHz Ultrasound and Microbubble Contrast Agent Treatments in Vivo." Ultrasound in Medicine & Biology, vol. 31, No. 4: 553-564, 2005.

(56) References Cited

OTHER PUBLICATIONS

Hynynen et al., "Potential Adverse Effects of High-Intensity Focused Ultrasound Exposure on Blood Vessels in Vivo." Ultrasound in Medicine & Biology, vol. 22, No. 2: 193-201, 1996.
Iannuzzi et al., "Ultrasonographic Correlates of Carotid Atherosclerosis in Transient Ischemic Attack and Stroke." Stroke, ProQuest Medical Library, vol. 26, No. 4: 614-619, 1995.
Idell et al., "Fibrin Turnover in Lung Inflammation and Neoplasia." American Journal of Respiratory and Critical Care Medicine, vol. 163: 578-584, 2001.
Indman, Paul. "Alternatives in Gynecology." Hysteroscopy, OBGYN.net, Oct. 14, 2004. http://www.gynalternatives.corn/hsc.html.
International Preliminary Report on Patentability dated Jun. 5, 2003 for PCT Application No. PCT/US00/35262.
International Search Report and Written Opinion dated Apr. 23, 2001 for PCT Application No. PCT/US00/35262.
International Search Report and Written Opinion dated Aug. 4, 2005 for PCT Application No. PCT/US2005/001893.
International Search Report and Written Opinion dated Jul. 11, 2007 for PCT Application No. PCT/US2006/041163.
International Search Report and Written Opinion dated Jun. 30, 2008 for PCT Application No. PCT/US2007/087310.
International Search Report and Written Opinion dated Mar. 30, 2007 for Application No. PCT/US2006/027688 filed on Jul. 13, 2006.
International Search Report and Written Opinion dated May 18, 2001 for PCT Application No. PCT/US00/41606.
International Search Report and Written Opinion dated May 29, 2007 for PCT Application No. PCT/USO4/31506.
Invitation to Pay Additional Fees and Partial International Search Report dated Nov. 29, 2006 for PCT Application No. PCT/US2006/027688.
Janssen, BJ and Smits, J. Renal Nerves in Hypertension. Mineral and Electrolyte Metabolism. 1090; 15:74-82.
Jolesz, F. MRI-Guided Focused Ultrasound Surgery. Annual Review of Medicine. 2009 60: 417-30.
Kaczkowski et al., "Development of a High Intensity Focused Ultrasound System for Image-Guided Ultrasonic Surgery." Ultrasound for Surgery, Oct. 14, 2004. (http://cimu.apl.washington.edu/hifusurgerysystem.html).
Kang et al., "Analysis of the Measurement Precision of Arterial Lumen and Wall Areas Using High-Resolution MRI." Magnetic Resonance in Medicine, vol. 44: 968-972, 2000.
Klibanov et al., "Detection of Individual Microbubbles of an Ultrasound contrast Agent: Fundamental and Pulse Inversion Imaging." Academy of Radiology, vol. 9, Suppl. 2: S279-S281, 2002.
Kojima, T., Matrix Array Transducer and Flexible Matrix Arry Transducer,Proceedings of the Ultrasonics Symposium, vol. 2:649-653 (1986).
Krum, H et. al. Catheter-Based Renal Sympathetic Denervation for Resistant Hypertension: a Multicentre Safety and Proof-of-Principle Cohort Study. Lancet 2009 373; 1275-81.
Krum, H. et. al. Pharmacologic Management of the Cardiorenal Syndrome in Heart FAilure. Current Heart Failure Reports 2009, 6: 105-111.
Kudo et al., "Study on Mechanism of Cell Damage Caused by Microbubbles Exposed to Ultrasound." Ultrasound in Medicine & Biology, vol. 29, Supplement: 4pp, 2003.
Lalonde et al., "Field conjugate acoustic lenses for ultrasound hyperthermia." Ultrasonics, Ferroelectrics and Frequency Control, IEEE Transactions, vol. 40, Issue 5: Abstract 1pg., Sep. 1993.
Martin et al., Hemostasis of Punctured Vessels Using Doppler-Guided High Intensity Ultrasound, Ultrasound in Med.& Biol., vol. 25, pp. 985-990, 1999, USA.
Meyers, D. "Multiresolution tiling." Computer Graphics, No. 5: 325-340, 1994.
Miller et al., "A Review of in Vitro Bioeffects of Inertial Ultrasonic Cavitation From a Mechanistic Perspective." Ultrasound in Medicine & Biology, vol. 22, No. 9: 1131-1154, 1996.

Miller et al., "Diagnostic ultrasound activation of contrast agent gas bodies induces capillary rupture in mice." PNAS, vol. 97, No. 18: 10179-10184, 2000.
Moss, Nicholas G. Renal Function and Renal Afferent and Efferent Nerve Activity. American Journal Physiology. 243 (Renal Fluid Electrolyte Physiology) 12: F425-F433, 1982.
n. a., "Breast Cancer—Insightec: focused ultrasound for non invasive treatment." FAQ, Oct. 14, 2004. (http://www.exablate2000.com/physicians_faq.html).
n. a., "Cavitation." Ultrasound TIP—U.S. Database: Dec. 12, 2007.
n. a., "Mechanical Bioeffects in the Presence of Gas-Carrier Ultrasound Contrast Agents." Journal of Ultrasound & Medicine, vol. 19: 120-142, 2000.
Ng et al., "Therapeutic Ultrasound: Its Application in Drug Delivery." Medicinal Research Reviews, vol. 22, No. 2: 204-233, 2002.
Notice of Allowance dated Mar. 25, 2003 from U.S. Appl. No. 09/696,076, filed Oct. 25, 2000.
Office Action dated Apr. 29, 2011 for U.S. Appl. No. 12/202,195.
Office Action dated Apr. 6, 2010 for U.S. Appl. No. 11/619,996.
Office Action dated Aug. 17, 2006 from U.S. Appl. No. 10/671,417, filed Sep. 24, 2003.
Office Action dated Feb. 18, 2011 for U.S. Appl. No. 11/583,656.
Office Action dated Jan. 7, 2011 for U.S. Appl. No. 12/762,938.
Office Action dated Jul. 14, 2009 for U.S. Appl. No. 11/619,996.
Office Action dated Jul. 31, 2007 from U.S. Appl. No. 10/671,417, filed Sep. 24, 2003.
Office Action dated Jul. 5, 2006 for U.S. Appl. No. 10/616,831.
Office Action dated Jul. 9, 2008 for U.S. Appl. No. 11/486,528.
Office Action dated Jun. 28, 2010 for U.S. Appl. No. 12/247,969.
Office Action dated Mar. 4, 2011 for U.S. Appl. No. 11/583,569.
Office Action dated Nov. 16, 2010 for U.S. Appl. No. 12/202,195.
Office Action dated Nov. 29, 2002 from U.S. Appl. No. 09/696,076, filed Oct. 25, 2000.
Office Action dated Oct. 19, 2009 for U.S. Appl. No. 11/486,526.
Office Action dated Oct. 19, 2009 for U.S. Appl. No. 11/583,256.
Office Action dated Sep. 16, 2010 for U.S. Appl. No. 11/583,656.
O'Leary et al., "Carotid-artery Intima and Media Thickness as a Risk Factor for Myocardial Infarction and Stroke in Older Adults." Cardiovascular Health Study Collaborative Research Group. New England Journal of Medicine, vol. 340, No. 1: 14-22, Jan. 7, 1999.
Ostensen et al., "Characterization and Use of Ultrasound Contrast Agents." Academy of Radiology, vol. 9, Suppl. 2: S276-S278, 2002.
Owaki et al., "The Ultrasonic Coagulating and Cutting System Injuries Nerve Function." Endoscopy, vol. 34, No. 7: 575-579, 2002.
Pernot, et al., "Temperature Estimation Using Ultrasonic Spatial Compound Imaging", IEEE Transactions on Ultrasonics, Ferroelectrics, and Frequency Control, (May 2004) 51(5):606-615.
Pignoli et al., "Intimal plus medial thickness of the arterial wall: a direct measurement with ultrasound imaging." Circulation, vol. 74, No. 6:1399-1406, Dec. 1986.
Poliachik et al., "Activation, Aggregation and Adhesion of Platelets Exposed to High-Intensity Focused Ultrasound." Ultrasound in Medicine & Biology, vol. 27, No. 11: 1567-1576, 2001.
Poliachik et al., "Effect of High—Intensity Focused Ultrasound on Whole Blood With or Without Microbubble Contrast Agent." Ultrasound in Medicine & Biology, vol. 25, No. 6:991-998, 1999.
Porter et al., "Ultrasound, Microbubbles and Thrombolysis." Progress in Cardiovascular Diseases, vol. 44, No. 2: 101-110, Oct. 2001.
Recchia et al., Ultrasonic Tissue Characterization of Blood during Stasis and Thrombosis with a Real-Time Linear-Array Backscatter Imaging System., Coronary Artery Disease, 1993, 4:987-994.
Rivens et al., "Vascular Occlusion Using Focused Ultrasound Surgery for Use in Fetal Medicine." European Journal of Ultrasound, vol. 9: 89-97, 1999.
Rose, Joseph, "Source Influence" Ultrasonic Waves in Solid Media, pp. 200-227, Cambridge University Press, 1999, USA.
Rosen et al., "Vascular Occlusive Diseases." 37pp., revised 2002.
Rosenschein et al., "Shock-Wave Thrombus Ablation, A New Method for Noninvasive Mechanical Thrombolysis." The American Journal of Cardiology, vol. 70, Issue 15: Abstract, Nov. 15, 1992.

(56) References Cited

OTHER PUBLICATIONS

Rosenschein et al., "Ultrasound Imaging-Guided Nonivasive Ultrasound Thrombolysis-Preclinical Results." Circulation, vol. 102: 238-245, 2000. (http://www.circulationaha.com.org).

Sanghvi et al. "High-Intensity Focused Ultrasounds." Experimental and Investigational Endoscopy. 4(2):383-395 (1994).

Schlaich, MP. Sympathetic Activation in Chronic Renal Failure. Journal American Society Nephrology 20: 933-939, 2009.

Schulte-Altedorneburg et al., "Accuracy of in Vivo Carotid B-Mode Ultrasound Compared with Pathological Analysis: Intima-Media Thickening, Lumen Diameter, and Cross-Sectional Area." Stroke, vol. 32, No. 7: 1520-1524, 2001.

Sheahan et al., Observing the Bracial Artery through a Pressure Cuff, Physiol. Meas. 14 (1993) 1-6.

Sherrit et al., the Characterisation and Modelling of Electrostrictive Ceramics for Transducers, Ferroelectrics, 228:(1-4), pp. 167-196, 1999.

Shrout et al., Classification of Electrostrictive-Based Materials for Transducers.

Shung, et al., "Ultrasonic Characterization of Blood During Coagulation", J. Clin. Ultrasound, (1984) 12:147-153.

Simon, et al, "Two-Dimensional Temperature Estimation Using Diagnostic Ultrasound", IEEE Transactions on Ultrasonics, Ferroelectrics, and Frequency Control, (Jul. 1998) 45(4):1088-1099.

Tachibana et al., "Albumin Microbubble Echo-Contrast Material as an Enhancer for Ultrasound Accelerated Thrombolysis." Circulation, vol. 92: 1148-1150, 1995.

Tachibana et al., "The Use of Ultrasound for Drug Delivery." Echocardiography, vol. 18, No. 4: 323-328, May 2001.

Tardy et al., "In Vivo Ultrasound Imaging of Thrombi Using a Target-specific Contrast Agent." Academy of Radiology, vol. 9, Suppl. 2: S294-S296, 2002.

ter Haar. G. Ultrasound Focal Beam Surgery. Ultrasound in Medicine and Biology. 21(9):1089-1100 (1995).

Vaezy ET Al., "Hemostasis of Punctured Blood Vessels Using High Intensity Focused Ultrasound," Ultrasound in Med.& Biol., vol. 24, No. 6, pp. 903-910,1998, USA.

Vaezy et al., "Acoustic surgery." Physics World: 35-39, Aug. 2001.

Vaezy et al., "Hemostasis and Tumor Treatment using High Intensity Focused Ultrasound: Experimental Investigations and Device Development." First International Workshop on the Application of HIFU in Medicine: 46-49, 2001.

Vaezy et al., "Hemostasis using high intensity focused ultrasound." European Journal of Ultrasound, vol. 9: 79-87, 1999.

Vaezy et al., "Intra-operative acoustic hemostasis of liver: production of a homogenate for effective treatment." Ultrasonics, vol. 43: 265-269, 2005.

Vaezy et al., Use of High-Intensity Focused Ultrasound to Control Bleeding, Mar. 1999, J Vasc Surg, vol. 29, pgs. 533-542.

Valente, JF et. al. Laparoscopic Renal Denervation for Intractable ADPKD Related Pain. Nephrology Dialysis and Transplantation. 2001 16:160.

Von Land et al., "Development of an Improved Centerline Wall Motion Model." IEEE: 687-690, 1991.

Watkin et al., "Multi-Modal Contrast Agents: A First Step." Academy of Radiology, vol. 9, Suppl. 2: S285-S287, 2002.

Wickline et al., "Blood Contrast Enhancement with a Novel, Non-Gaseous Nanoparticle Contrast Agent." Academy of Radiology, vol. 9, Suppl. 2: S290-S293, 2002.

Williamson et al., "Color Doppler Ultrasound Imaging of the Eye and Orbit." Survey of Ophthamology, vol. 40, No. 4: 255-267, 1996.

Yu et al., "A microbubble agent improves the therapeutic efficiency of high intensity focused ultrasound: a rabbit kidney study." Urological Research, PubMed: Abstract, 2004.

\* cited by examiner

CONTROLLED HIGH EFFICIENCY LESION FORMATION USING HIGH INTENSITY ULTRASOUND

RELATED APPLICATIONS

This application is a continuation of U.S. application Ser. No. 10/633,726, filed Aug. 4, 2003, which is a continuation of U.S. application Ser. No. 09/721,526, filed Nov. 22, 2000, now U.S. Pat. No. 6,626,855, which claims the benefit of U.S. Provisional Application No. 60/167,707, filed Nov. 26, 1999, all of which are incorporated herein by reference in their entirety.

FIELD OF THE INVENTION

This invention relates generally to methods and apparatus for efficiently heating biological tissues with high intensity ultrasound for therapeutic purposes, and in particular, to endoscopic devices for applying ultrasound energy to uterine fibroids and other pathologic tissues that are inside body or organ cavities, to destroy the tumor or the diseased tissue.

BACKGROUND OF THE INVENTION

Fibroids are benign tumors in women's uteri. There are different types of fibroids, including submucosal, which are inside the uterine cavity; intramural, which are in the uterine wall; and subserosal, which are outside the uterus. Fibroids may cause excessive bleeding and pain. For symptomatic fibroids, surgery is the predominate treatment. Every year in the U.S., there are more than 200,000 cases of fibroid-caused hysterectomies. To preserve the uterus, the patient may choose myomectomy, which removes the fibroids only. There are more than 80,000 abdominal myomectomies each year in the U.S. These surgical procedures cause significant trauma to the patients and result in significant costs. Consequently, patients need several days of hospital stay and suffer from the prolonged recovery.

Minimally invasive surgical (MIS) procedures have been explored to treat uterine fibroid trans-abdominally or trans-cervically under laparoscopic or hysteroscopic guidance. Many MIS apparatus have been developed to make the procedure less difficult. Several prior art devices are described in U.S. Pat. No. 5,304,124; U.S. Pat. No. 5,662,680; and U.S. Pat. No. 5,709,679. Besides surgically resecting and removing the tumor tissue, alternative treatments include using different energy forms, such as laser, radio frequency (RF), and cryo-therapy, to thermally ablate or necrose the fibroid tissue. Most of these techniques require the insertion of needles or other types of devices into the body of the fibroid. The mechanical damage to the fibroid and the uterus can cause bleeding during the treatment and adhesions after the treatment. Suturing the damage in the uterus is very difficult in the laparoscopic MIS procedure. Also, most of these alternative treatments are time consuming and technically challenging.

Uterine arterial embolization (UAE) has been investigated as an alternative treatment for uterine fibroids. In UAE, a catheter is inserted into the patient's femoral artery. The catheter is then advanced until its tip reaches the uterine artery. Many small particles are then injected into the uterine artery to block the blood flow. Both left and right uterine arteries are treated. Blood vessels supplying uterine fibroids are typically larger than the vessels in the normal uterine tissue. With properly sized particles, the blood vessels feeding the uterine fibroids are embolized, but not those in the normal uterine tissue. The fibroids then starve and die due to lack of a blood supply. The uterus survives, however, on the blood supplied from the ovarian artery and other collateral circulation. The embolization procedure may cause severe pain in the first few days after the treatment. Other disadvantages of UAE may include long X-ray radiation exposure during the procedure and other long-term potential adverse effects. The procedure is not recommended if the patient seeks a future pregnancy.

Ultrasound is a term that refers to acoustic waves having a frequency above the high limit of the human audible range (i.e., above 20 KHz). Ultrasound waves have the capability of penetrating into the human body. Based on this property, ultrasound in the frequency range of 2-20 MHz has been widely used to image internal human organs for diagnostic purposes. Ultrasound imaging has also been suggested as a tool for guidance during a resectoscopic surgery (U.S. Pat. No. 5,957,849).

When ultrasound energy is absorbed by tissue, it becomes thermal energy, raising the temperature of the tissue. To avoid thermal damage to tissue, the power level in diagnostic ultrasound imaging is kept very low. The typical ultrasound intensity (power per unit area) used in imaging is less than 0.1 watt per square centimeter. High intensity focused ultrasound, which can have an intensity above 1000 watts per square centimeter, can raise the tissue temperature at the region of the spatial focus to above 60-80 degrees Celsius in a few seconds and can cause tissue necrosis almost instantaneously.

High intensity ultrasound has been proposed to treat and destroy tissues in the liver (G. ter Haar, "Ultrasound Focal Beam Surgery," Ultrasound in Medicine and Biology, Vol. 21, No. 9, pp. 1089-1100, 1995); in the prostate (N. T. Sanghvi and R. H. Hawes, "High-intensity Focused Ultrasound," Experimental and Investigational Endoscopy, Vol. 4, No. 2, pp. 383-395, 1994); and in other organs. In U.S. Pat. Nos. 5,080,101, 5,080,102, 5,735,796, 5,769,790, and 5,788,636, for example, ultrasound imaging is combined with a high intensity ultrasound treatment to target the treatment region and to monitor the treatment process. In U.S. Pat. Nos. 5,471,988, 5,492,126, 5,666,954, 5,697,897, and 5,873,828, endoscopic ultrasound devices with both imaging and therapeutic capabilities are disclosed. These devices all have an elongated tube or shaft, so that they can be inserted in organ cavities (e.g., into the rectum) or into the abdominal cavity through a puncture hole in the abdominal wall to bring the ultrasound imaging and treatment sources closer to the disease sites. Some of them have flexible ends, which can be bent to fit the anatomy of a specific patient.

The therapeutic ultrasound beam is focused inside tissue to a small spot of a few millimeters in size. At the focus, tissue temperature rapidly exceeds a level sufficient to cause tissue necrosis, thus achieving the desired therapeutic effect. Outside of the focus, ultrasound energy is less concentrated, tissue temperature rise remains below the necrosis level during the typically short exposure times employed. To treat a tissue volume larger than the focal spot, in the prior art, the ultrasound focus is deflected mechanically or electronically to scan, or incrementally expose, the target tissue volume. One disadvantage of the current high intensity ultrasound therapy is its inefficiency when treating large tumors or heating a large volume of tissue Even though a three-second ultrasound pulse can increase the temperature of tissue at its focus dramatically, the ultrasound treatment must typically pause 40-60 seconds between two subsequent pulses to allow the intermediate tissue between the focus and the ultrasound transducer to cool sufficiently to avoid thermally damaging the tissue. The volume of tissue necrosis for each treatment pulse is very small (~0.05 cm$^3$). For example, to treat a volume of tissue within a 3 cm diameter sphere, it will take more than 4 hours, too long to be practical in most clinical situations. Many symptomatic uterine fibroids are larger than 2-3 cm in diameter, and multiple fibroids are also common. To be acceptable for clinicians and patients, the ultrasound treatment time must be significantly reduced.

Large device size is the second disadvantage of the therapeutic ultrasound apparatus in much of the prior art. Most of these devices have two separated ultrasound transducers, including one for imaging and the other for therapy. For effective treatment, the diameter of the treatment transducer is approximately equal to the maximum depth, where the f-number (transducer diameter divided by its focal length) of the transducer is about one (f/1). The transducer surface area must also be sufficiently large to generate high ultrasound power. In some prior art endoscopic devices (for example, in U.S. Pat. Nos. 5,471,988 and 5,873,828), there is a large orifice in the center of the therapy transducer for positioning an imaging transducer. This orifice reduces the area of the treatment transducer and increases its effective f-number. In this case, the size of the treatment transducer must be increased to maintain its effectiveness, so that the overall dimensions of the device are increased. For endoscopic (trans-cervical or trans-abdominal) uterine fibroid treatments, the maximum acceptable diameter of an ultrasound device is about 10 mm. It is seen that it is very difficult to meet this requirement with the large two-transducer configuration.

There is another disadvantage of the two-transducer configuration in which there is an orifice in the center of the treatment transducer. In endoscopic uterine fibroid treatment, the ultrasound device is directly brought against the surface of the fibroid tumor. The tumor surface near the orifice of the transducer will not be treated unless the transducer is moved away or aside from its initial position. Oftentimes, the space is very limited, especially inside the uterus. There may not be sufficient space to permit the device to move, a limitation that results in incomplete treatment of the tumor.

What is needed is a minimally invasive or noninvasive device for treating uterine fibroids. The device should preferably cause minimal or no trauma to the patient body so that the patient requires minimum or no recovery time; it should be easy to use; and, the treatment should be quickly administered. The device should preferably not cause blood loss during the treatment procedure; it should not mechanically damage the treated organ (e.g. uterus) to avoid the need for complicated organ repair (such as suturing or extensive cauterization); and, it should not increase the risk of post-operative adhesions and other complications. In addition, the device should be capable of carrying out the following functions:

(1) Ultrasonically increase the tissue temperature in the uterine fibroid to cause tumor necrosis. Shrinkage of the necrosed tissue will reduce the blood supply to the tumor. This occlusion effect will further reduce the chance of survival for the tumor.
(2) Significantly reduce the ultrasound treatment time and thereby improve physician and patient acceptance. A positive feedback heating process can be provided to efficiently and rapidly raise the temperature in a large volume of tissue.
(3) Combine the ultrasound imaging and therapy transducer in one to enable the dimensions of the apparatus to be more compact so that the device can be inserted into patient's uterine cavity or permit practical laparoscopic use (e.g., be inserted trans-abdominally).
(4) Include a treatment transducer that does not have an orifice in its center, so that the tumor tissue can be treated thoroughly.
(5) Provide ultrasound imaging capability for treatment guidance. The imaging capability should provide real-time assessment of the anatomy before, during, and after the treatment. Doppler imaging can be advantageously employed to aid targeting and the assessment of treatment.
(6) Use ultrasound to detect and differentiate the tissue property changes before and after the treatment to make an assessment of the treatment result possible.
(7) Create an acoustic absorption barrier inside the treated tissue to prevent the tissue beyond the desired treatment zone from being thermally damaged.
(8) Provide a feedback control mechanism to turn the treatment transducer element off when the transducer is not properly coupled to the tissue to prevent the device from being damaged by reflected ultrasound power.
(9) Provide an effective cooling mechanism to prevent the device from being thermally damaged.
(10) Use an ultrasound contrast agent (micro-bubbles) to enhance the treatment effect.
(11) Provide effective means to acoustically couple an ultrasound source to targeted tissue structures.
(12) Use elasticity imaging to assess the state of tissues prior, during, and after ultrasonic treatment.
(13) Employ cavitation as a therapeutic means to necrose selected tissues.

Currently, an endoscopic ultrasound probe is not available that can provide the above-noted functions. Accordingly, it will be apparent that both such a device and an effective and efficient method for treating uterine fibroid tumors and other internal tissues and diseased tissue masses is needed that overcomes the problems with prior art apparatus and methods.

SUMMARY OF THE INVENTION

The present invention is directed to a method and apparatus for efficiently treating uterine fibroids and other diseases with high intensity ultrasound, where the apparatus is small enough to fit in the limited space in a patient organ cavity or a limited puncture size on an abdominal wall.

Specifically, an ultrasonic system for destroying undesired tissue at an internal site within a body of a patient includes a probe that is sized to be inserted within a body of a patient. An ultrasonic transducer is mounted proximate a distal end of the probe and is adapted to couple to a power supply used to selectively energize the ultrasonic transducer so that it produces a focused beam of high intensity ultrasonic energy. An ultrasound transmissive interface is coupled to the distal end of the probe and is disposed and adapted to conform to a surface of the undesired tissue. The interface provides a liquid layer that more efficiently transmits the high intensity ultrasonic energy produced by the ultrasonic transducer into the undesired tissue. The high intensity ultrasonic energy increases a temperature of the undesired tissue sufficiently to cause the tissue to necrose.

In one form of the invention, the ultrasound transmissive interface comprises an elastomeric cavity that is adapted to contain a liquid. The elastomeric cavity is disposed between the ultrasonic transducer and the surface of the undesired tissue so that the high intensity ultrasonic energy passes through the liquid within the elastomeric cavity and into the undesired tissue. The elastomeric cavity is formed at least in part from a semi-permeable membrane, so that the liquid from within the elastomeric cavity weeps onto a surface of undesired tissue to increase the efficiency with which the high intensity ultrasonic energy is coupled into the undesired tissue.

In another form of the present invention, the ultrasound transmissive interface comprises a cap made of an elastomeric material, which is disposed to surround the ultrasonic transducer. The cap is adapted to seal against the undesired tissue and to contain a liquid that increases an efficiency with which the high intensity ultrasonic energy is coupled into the undesired tissue. In addition, the cap preferably includes a rim having a double lip seal formed around a perimeter. A passage in the cap is adapted to couple the double lip seal to a vacuum line so that the rim of the cap is held against a surface of the undesirable tissue, sealing the liquid inside of the cap.

Another aspect of the present invention is directed to a method for administering an ultrasonic therapy to destroy at least a portion of an undesired tissue mass. The method includes the steps of providing an ultrasonic transducer that emits a focused high energy ultrasonic energy when energized, and positioning the ultrasonic transducer proximate the undesired tissue mass. The ultrasonic transducer is directed toward a desired focal point within the undesired tissue mass. Then, the ultrasonic transducer is energized so that it emits the focused high energy ultrasonic energy at the desired focal point, causing necrosis of a portion of the undesired tissue mass disposed at the desired focal point. At least one of an f-number, an intensity, a time, and a direction of the high intensity ultrasonic energy emitted into the undesired tissue mass is controlled to achieve a desired shape and size of a necrotic zone of undesired tissue, destroyed as a result of being heated by the high intensity ultrasonic energy. The necrotic zone substantially blocks the high intensity ultrasonic energy from penetrating beyond the necrotic zone. The desired shape and size of the necrotic zone are preferably selected and formed so as to cause substantially of the undesired tissue mass to ultimately be destroyed.

The step of controlling preferably includes the step of repositioning the ultrasonic transducer to direct the high intensity ultrasonic energy at a different portion of the undesired tissue mass, to achieve the desired shape and size of the necrotic zone. In one application of the method, the desired shape and size of the necrotic zone are selected so that formation of the necrotic zone substantially deprives the undesired tissue mass of a blood supply, causing the ultimate destruction of the undesired tissue mass. In another application of the method, the desired shape and size of the necrotic zone are selected to control bleeding at a treatment site.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

In the following description of the present invention, its application in treating uterine fibroid tumors is discuss in some detail. However, it should be emphasized that the device and methods described herein may also be used to apply ultrasound therapy treatment to other organ systems, lesions, and disease states. The therapy delivered may be thermal ablation, where a temperature rise is established to a level at which tissues are no longer viable; mechanical ablation, where cavitation is employed as the primary ablative means; or may achieve hemostasis wherein bleeding or blood flow in intact organs is arrested. Such applications of the present invention may be accomplished in open, invasive surgery, by way of established minimally invasive techniques (for example, by way of body entry through one or more small incisions or punctures), or in some cases, noninvasively, through the skin surface or through the linings of body cavities such as the rectum, vagina, or esophagus. Ablative treatment with the present invention may be applied to a wide range of benign or cancerous lesions of the liver, kidney, pancreas, spleen, prostate, breast, bowel, rectum or similar organ systems, wherein the device described herein may be placed in close proximity to the disease location. Also, acoustic hemostasis treatment may be employed to deprive a disease lesion of its blood supply or used to facilitate surgical procedures by arresting bleeding or blood flow.

Many tumors, such as uterine fibroids, locate superficially inside or outside the organ. During hysteroscopic or laparoscopic surgeries, surgeons can easily reach the surfaces of those tumors with an intra-cervical or intra-abdominal instrument. For an ultrasound transducer at the tip of the intra-cavity instrument touching the tumor directly, there will be little or no intermediate tissue that needs to be spared and cooled, so that pauses in the treatment for this purpose may become unnecessary.

Figure 1:
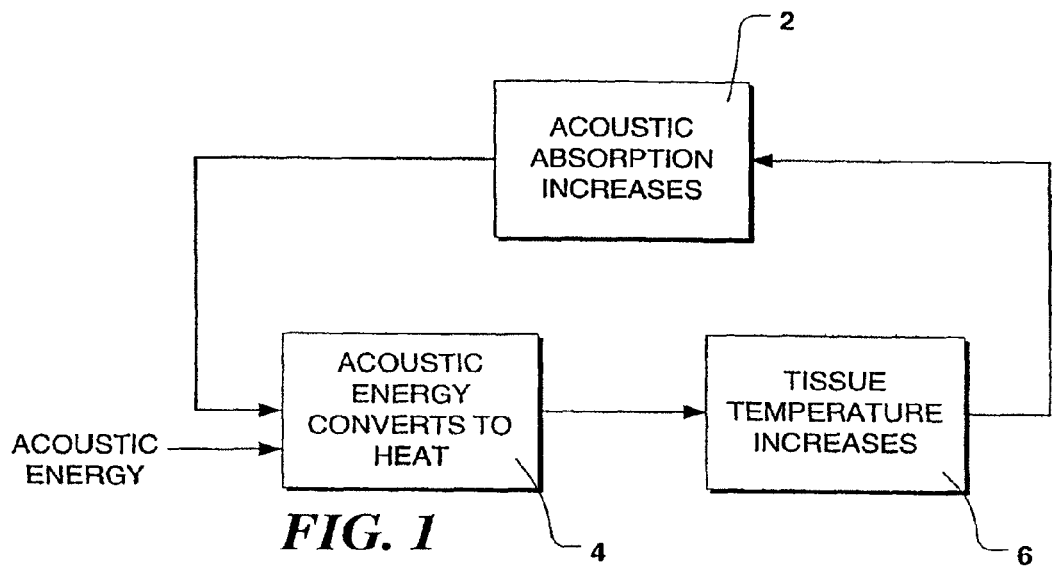
FIG. 1 is a block diagram of the positive feedback mechanism of the improved tissue heating process.
Figure 2A:
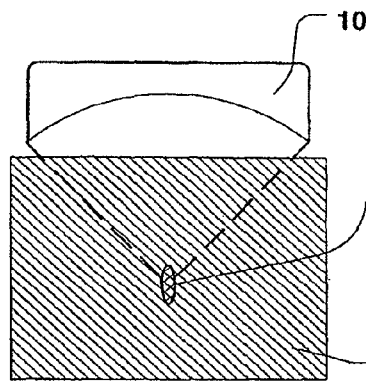
FIGS. 2A-2D illustrate different thermal lesion shapes.
Figure 2B:
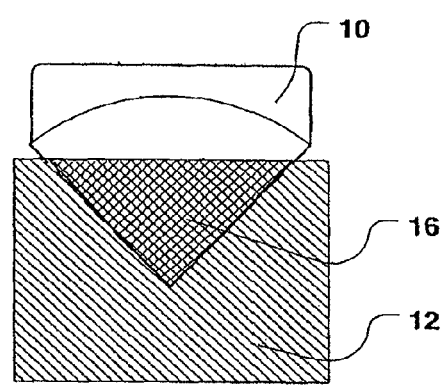

According to conventional wisdom, the pre-focal heating is considered to be a negative effect and needs to be minimized. In the case of intra-cavity treatment of uterine fibroids, however, this pre-focal heating can provide significant enhancement to the efficiency of tissue heating when the ultrasound transducer can be disposed in close contact with the tumor surface. A positive feedback mechanism of tissue heating (illustrated in FIG. 1) is preferably used to improve the efficiency of the treatment provided by the present invention. The positive feedback indicated by a block 2 of FIG. 1 enhances acoustic absorption. The acoustic energy is converted to heat, as noted in a block 4, resulting in a greater temperature rise in the tissue, as indicated in a block 6. Tissue acoustic absorption increases significantly when its temperature rises above 50° C. Referencing FIG. 2A, a small f-number, high intensity ultrasound transducer 10, running in continuous-wave (CW) mode, raises the temperature in tissue 12 at its focus to 70-90° C. in less than two seconds and forms a small lesion 14. This isolated thermal lesion serves two purposes. First, it is the initial seed to start the positive feedback heating process; and, secondly, its high acoustic absorption blocks ultrasound energy from penetrating beyond the focal depth to cause undesirable damage to normal tissue. In an experimental study, it was observed that after the lesion started at the focus, it first grew along the central axis of the transducer and towards the transducer to form an elongate lesion. Then, the end of the elongate lesion closer to transducer began growing laterally wider. Eventually, the lesion became a wedge shape 16 (FIG. 2B). The tissue layer near the surface, adjacent to transducer 10, was the last portion to necrose.

In an experimental study, a wedge-shaped lesion of tissue necrosis was generated with this mechanism by running the ultrasound power continuously, while keeping the transducer position fixed. The volume of the thermal lesion was about 4.5 cm$^3$, and the treatment time was approximately two minutes. The average treatment rate was about 2.25 cm$^3$/min, which was 45 times faster than provided by a conventional pulse-pause treatment strategy.

Figure 2C:
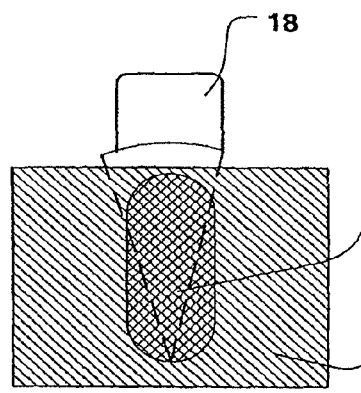
Figure 2D:
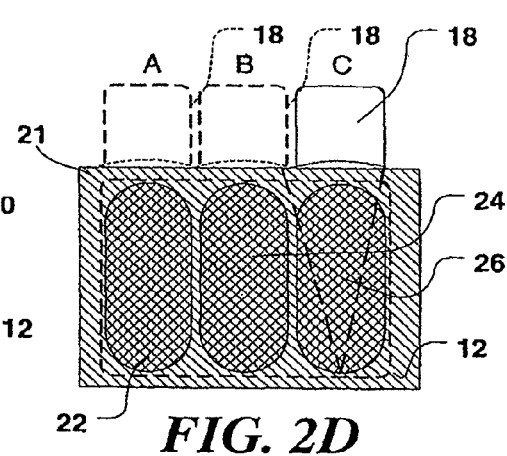

Using the present invention, the size and the shape of the large thermal lesion can be readily controlled. To form a thin elongate lesion column 20 in the tissue (FIG. 2C), a circular transducer 18 with a relatively large f-number (~2) is used to treat the tissue over a relatively short time. To create a conical shaped lesion, a circular transducer with a small f-number (~1) is used to treat the tissue for a relatively long time. To form a thin, wedge-shaped lesion, i.e., shaped like a slice of pie (FIG. 2B), a cylindrical or truncated circular transducer is used to treat the tissue over a relatively long time. A generally rectangular lesion plane 21 (FIG. 2D) can be generated by forming a row of tightly spaced lesion columns 22, 24, and 26. Each column is formed from a fixed transducer position in a short time. The transducer may then be quickly shifted laterally to generate the next adjacent column, moving from position "A" to "B" to "C" as shown in FIG. 2D. Thermal diffusion in the tissue fuses the columns together to form rectangular lesion plane 21. It is also possible to create a large lesion in the tissue without damaging the organ surface. One approach is to cool the tissue surface with circulating water or saline. The other approach is to use an attenuation measurement technique described below, to monitor lesion progress (growth) and control power, accordingly.

Figure 3A:
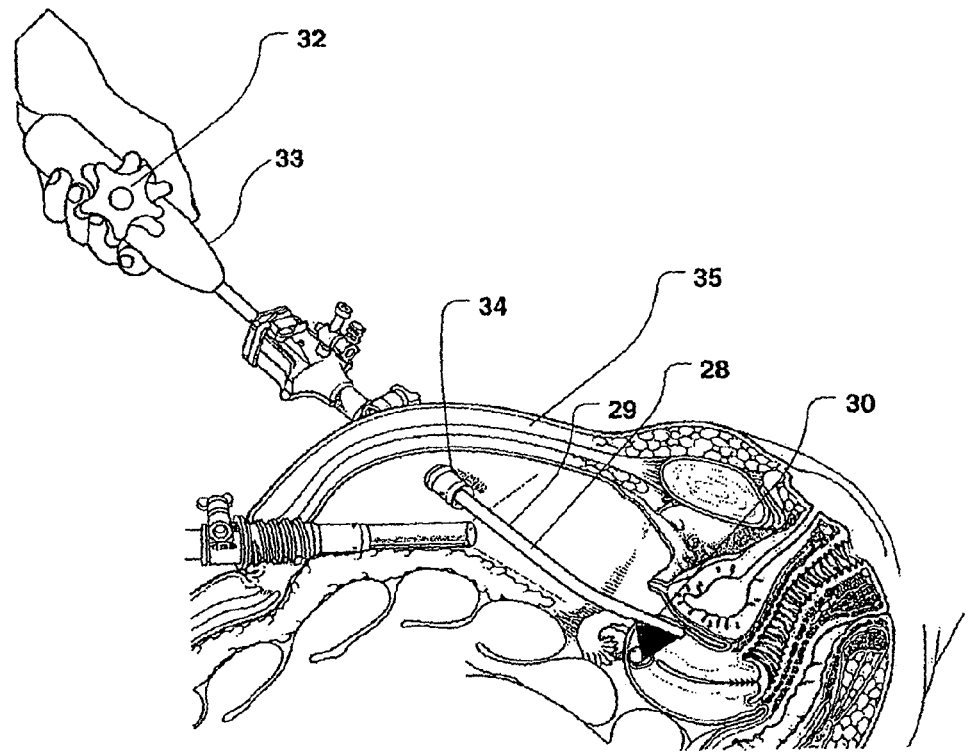
FIG. 3A is a cross-sectional view of a portion of a patient's body, illustrating application of an endoscopic device in accord with the present invention, which can both acquire ultrasound images and generate high intensity therapeutic ultrasound at its distal end.
Figure 3B:
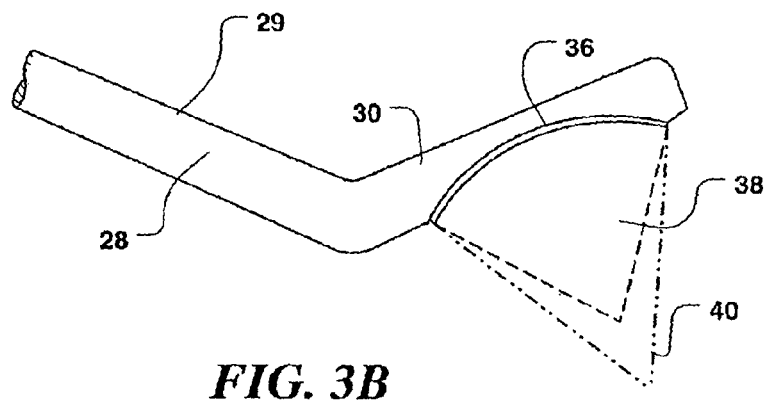
FIGS. 3B and 3C are side elevational views of a portion of the device shown in FIG. 3A, illustrating an imaging field and a treatment field of the device.

The basic concept and configuration of a high intensity ultrasound device 29 in accord with the present invention are shown in FIGS. 3A and 3B. The device has a thin, elongate shaft 28 that can be inserted through the cervix into the uterine cavity, or, as shown in FIG. 3A, through a laparoscopic opening 34 in the abdominal wall and into the abdominal cavity. A distal end 30 of the shaft contains a concave-shaped ultrasound transducer array 36 (FIG. 3B) and may be formed into different curves to fit different anatomies of individual patients. The distal end that is thus formed can be permanently fixed or articulated by turning a control knob 32 on a handle 33 of the device. Transducer array 36 in FIG. 3B is operable for both ultrasound imaging and treatment. To form an ultrasound image, the transducer array generates ultrasound pulses and receives echoes from the imaged anatomy in a cross-sectional area 40. The two-dimensional (2D) ultrasound image displays the cross-sectional view of the anatomy. The image can be updated rapidly in real-time with a frame rate of, for example, 10-30 frames per second. Physicians can then view this real-time image to locate the tumor or other tissue that needs to be treated or spared from treatment. When the treatment area is identified in the image, the transducer array is employed to generate high intensity ultrasound focused in a treatment area 38. After the tissue in the treatment area has been necrosed, the distal end of the ultrasound device is moved to a new location to sequentially treat another part of the tumor tissue. The imaging and the treatment are interleaved in time so that the treatment process and the progress of the treatment may be monitored.

Doppler flow imaging (spectral Doppler or power mode Doppler) may be utilized to assist targeting and to monitor treatment effects and to determine the endpoint of the therapy. Imaging blood flow is particularly useful when a blood flow occlusion strategy is being utilized, since the cessation of blood flow can be directly monitored. Doppler imaging facilitates localization of the vascularity typically surrounding uterine fibroid tumors or other tumor masses.

There are many possible combinations of the imaging and treatment capabilities. Imaging and therapy may be one-, two-, or three-dimensional in various combinations; scan geometries may be fixed or selectable; and imaging and therapy may proceed either simultaneously or sequentially in time. A preferred embodiment of the ultrasound intra-cavity device discussed herein has the capability to carryout 2D real-time imaging and the capability to produce tissue necrosis in a substantially 2D slice (thickness of this slice is nominally less than one centimeter). Including the lesion-control techniques discussed above, there are many ways to control treatment geometry with this device. Different spatial beam patterns can be generated from by the ultrasound transducer array included on the device to form a specific lesion shape, or potentially, to reduce treatment time. Multiple sequential exposures of different spatial beam patterns can also be used to control the treatment dosage at different locations to form lesion shapes that cannot be generated by fixed beam patterns.

Figure 6:
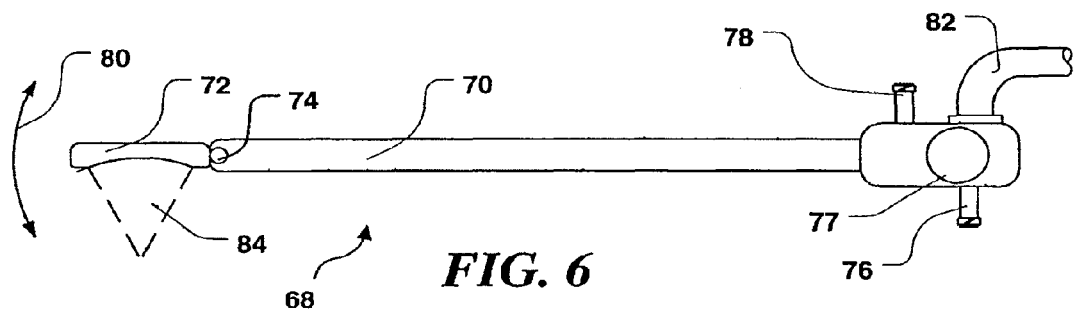
FIG. 6 is a schematic diagram of the trans-cervical ultrasound device with an articulated end.

As shown in FIG. 6, a trans-cervical ultrasound device 68 is adapted to treat submucosal fibroids. The device is inserted into a patient's uterine cavity through the vagina and the cervical canal. The uterine cavity is distended with sterile water or saline under 50-80 mm Hg pressure delivered through internal channels inside a shaft 70 of the device and connected to couplings 78 and 76. The water provides working space for manipulation of the device, and the water thus infused also serves as a transducer coupling and cooling medium.

The fibroid is visualized by ultrasound imaging using trans-cervical ultrasound device 68. As a function of the tumor size and shape, the physician selects the appropriate treatment geometry and turns the therapeutic ultrasound power on to necrose a slice volume of the tumor tissue in front of the transducer. The entire tumor is then treated typically piece by piece. During the treatment, the transducer (not separately shown) at a distal end 72 of the device does not have to directly contact the tumor surface—the water in the uterus is a good acoustic coupling and transmission medium. After the tumor is completely treated, the physician removes the device and drains the water from the patient's uterus. The procedure is finished without any surgical invasion to the tissue.

Figure 7A:
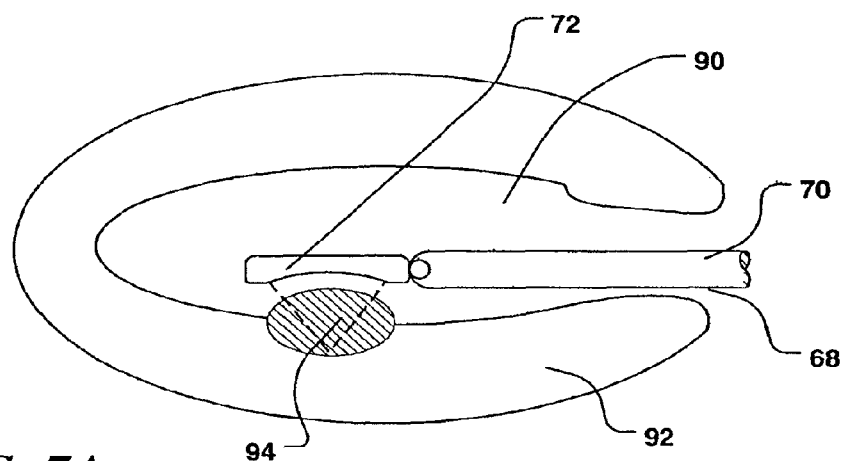
FIGS. 7A and 7B are schematic diagrams showing transcervical hemostasis treatment performed in combination with resectoscopic removal of submucosal fibroids.
Figure 7B:
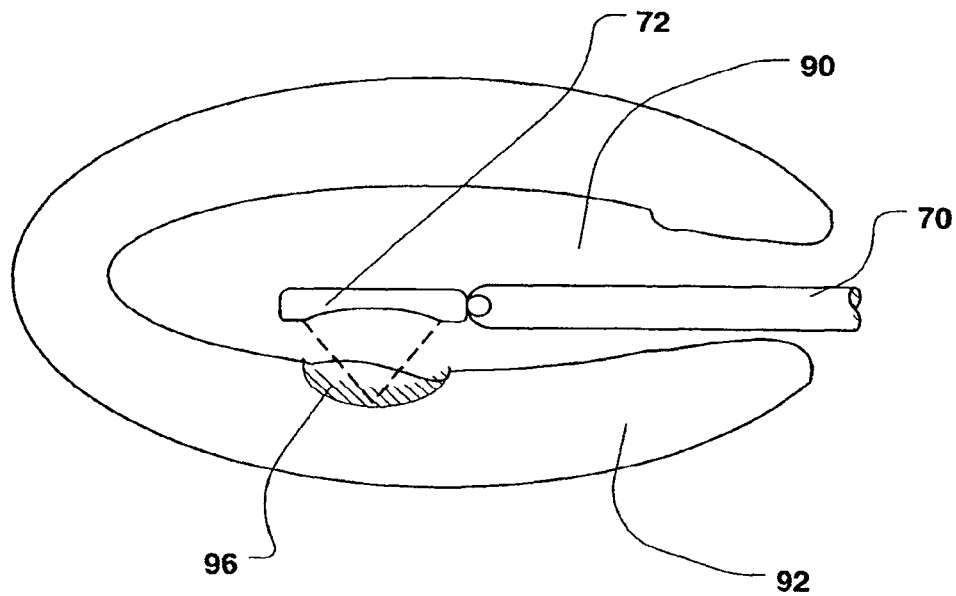

There are two possible approaches for providing treatment of a submucosal fibroid tumor 94 with trans-cervical ultrasound device 68. The physician can treat the whole tumor directly with the ultrasound device, as shown in FIG. 7A, or treat only a remaining tumor base 96, as shown in FIG. 7B, after a portion of the tumor is removed by using a resectoscope. In FIG. 7A the transducer in distal end 72 is placed adjacent to tumor 94 inside a water-filled uterine cavity 90. For the latter approach, the ultrasound device works not only as an ablation tool, but also as a hemostasis tool to seal off the open, bleeding vessels around and inside the exposed tumor base.

Figure 8A:
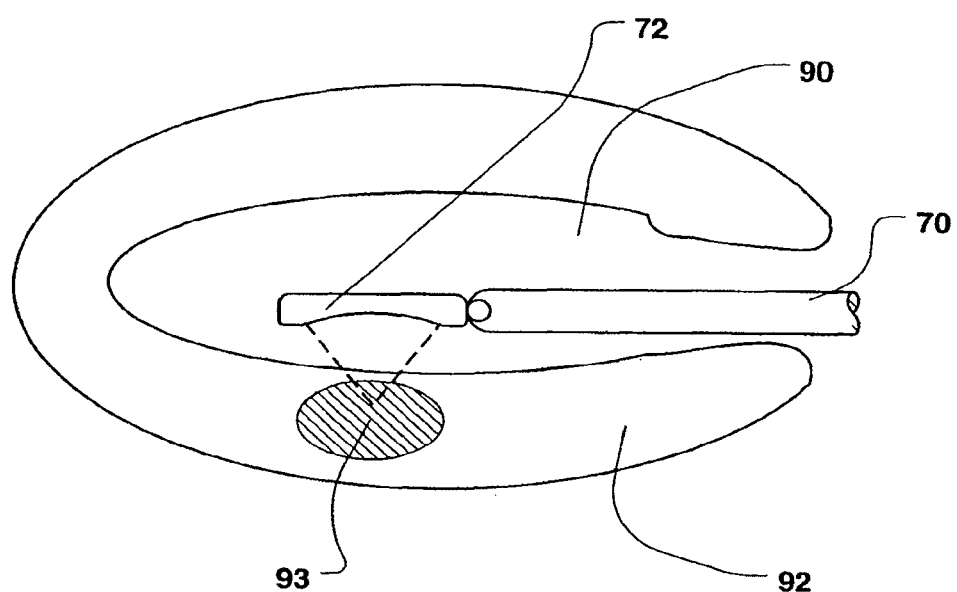
FIGS. 8A and 8B are schematic diagrams respectively showing the trans-cervical and the trans-abdominal ultrasound device treating intramural fibroids from inside and from outside of the uterus.
Figure 8B:
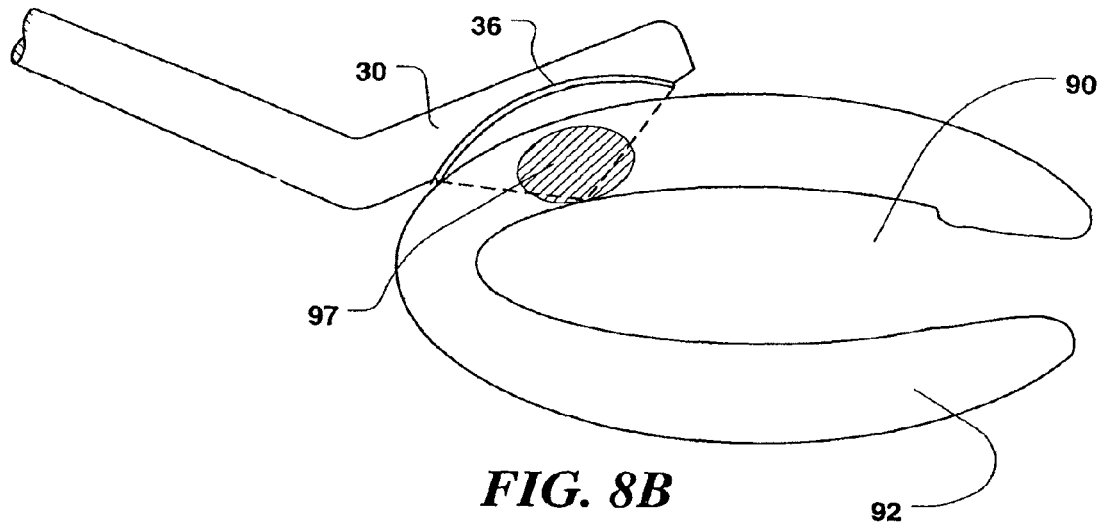

A similar technique may be used to treat intramural fibroids as illustrated in FIGS. 8A and 8B. If a tumor 93 is closer to the inside of the uterus (FIG. 8A), a trans-cervical ultrasound device is the choice for the treatment. Otherwise, a trans-abdominal device may be used (FIG. 8B). Some intramural fibroids 96 are imbedded inside normal uterine tissue, e.g., in a uterine wall 92. The physician may want only to necrose the tumor but not the uterine wall that covers the tumor. In this case, the physician can use the lesion geometry control techniques described above to heat only the tumor inside the uterine wall without thermally damaging the surrounding tissue.

Figure 9A:
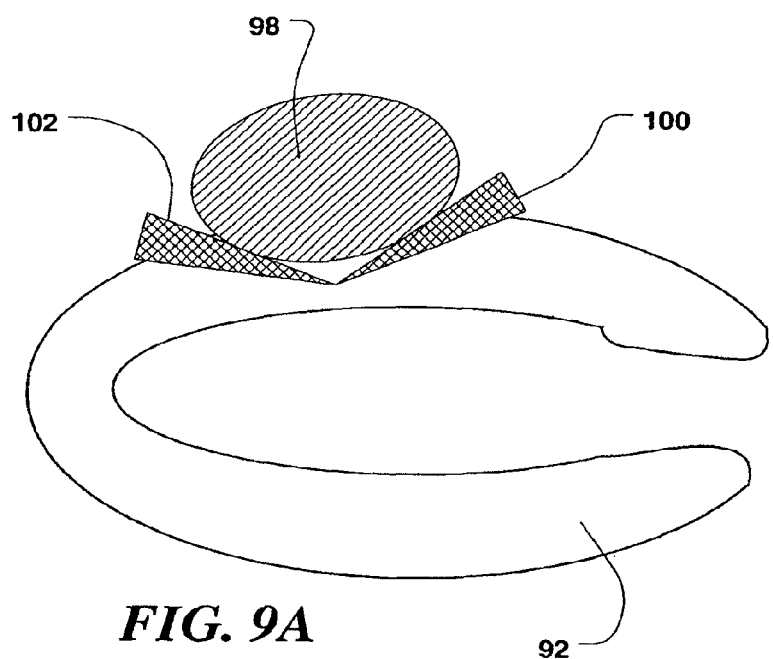
FIGS. 9A and 9B are schematic diagrams respectively showing laparoscopic occlusion treatment of subserosal fibroids, and a wedge of necrosed tissue produced thereby.
Figure 9B:
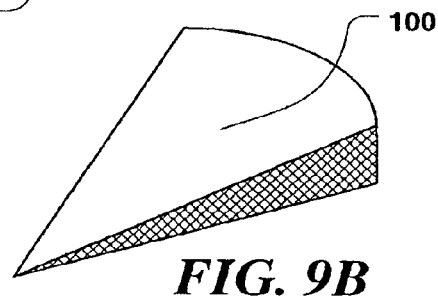

Subserosal fibroids are disposed substantially outside of the uterus. When these are symptomatic, they may be larger than submucosal and intramural fibroids. However, the trans-abdominal ultrasound device according to the present invention can also be used to treat them. If the physician uses the same treatment technique as described above to thermally necrose the entire tumor, it will take longer time, because they are relatively large. An alternative approach is shown in FIGS. 9A and 9B, where only the tumor base is treated by a series of sectors, or pie-shaped applications 100, 102 (FIG. 9B) that are circumferentially disposed around the base of a tumor 98. After the entire tumor base is heated sector by sector, the tumor tissue in the base shrinks. The tissue shrinkage occludes blood vessels in the base and achieves effective tumor starvation as oxygen and nutrient supplies are interrupted. Without a blood supply, the tumor will die. The necrosed tumor will then shrink in volume, so that the pressure symptoms experienced by the patient due to the growth of the tumor will be relieved.

Figure 10:
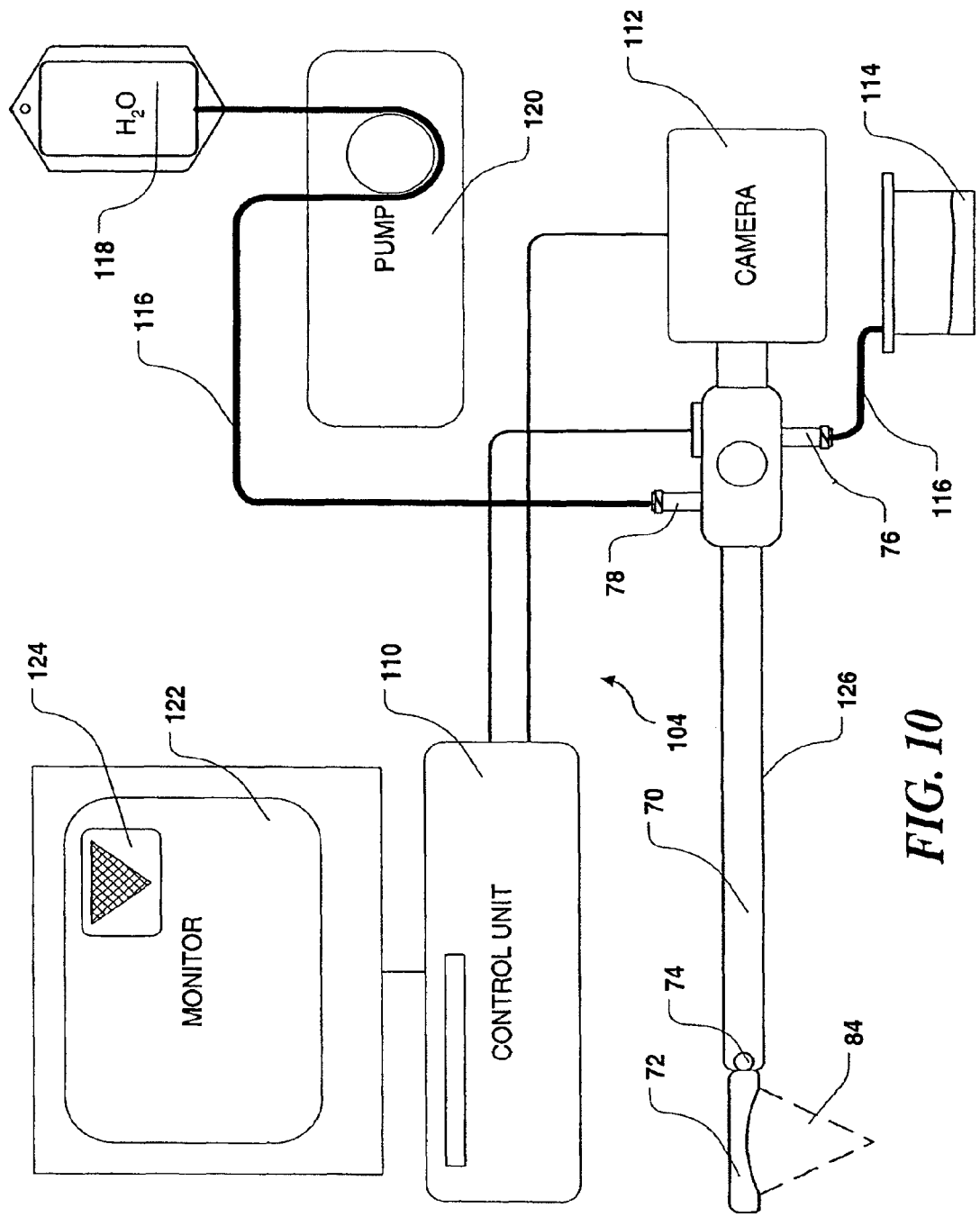
FIG. 10 is a block diagram of the trans-cervical ultrasound device connected with its control unit, display, and fluid management unit.

A system 104 that supports operation of trans-cervical ultrasound device 68 is shown in FIG. 10. The system consists includes one Or more ultrasound applicators 126, an optional optical hysteroscope (not separately shown), which is inside the applicator, and its associated camera 112, a treatment control unit 10, a TV monitor 122, and a fluid management system that includes a fluid management system pump 120, tubing 116, and a waste collection container 114. The hysteroscope, camera, monitor, and fluid management system are typically available in a well-equipped gynecology operating room. The optional hysteroscope may be useful for visually locating the tumor. Control unit 110 provides electronic signals and power to the ultrasound transducer for both imaging and therapy. The ultrasonic image and the optical image from the camera attached to the hysteroscope are combined in the control unit and are preferably displayed on the monitor in a "picture-in-a-picture" format 124. Alternatively, either one of the images may be displayed alone. Fluid management system pump 120 controls the saline or water pressure and the flow rate into the uterus.

Different configurations of the trans-cervical ultrasound device shown in FIG. 6 have specific advantages. They all have two irrigation channels for fluid in and out, one electrical cable to connect to the control unit, and one utility channel for the hysteroscope. The difference is in their tip configuration. In FIG. 6, the distal end of the applicator can bend to different angles 80 about a pivot 74, to accommodate different approaches to the treatment zone. A knob 77 at the device handle controls the tip articulation, providing an adjustable head angle over a range of up to 90 degrees. Alternatively, the distal end of the device may be fixed, and several applicators of different fixed tip angles can be provided for different treatments.

The ultrasound transducer in the end of the trans-cervical applicator may have a limited usable lifetime. The tip of the device may be a reposable (disposable, with a limited number of times of reuse). A used tip can thus be removed, and a new tip attached. The reposable portion may include shaft 70, so that the connection port will be in the handle, which stays outside the patient and is not immersed in fluid.

Figure 3C:
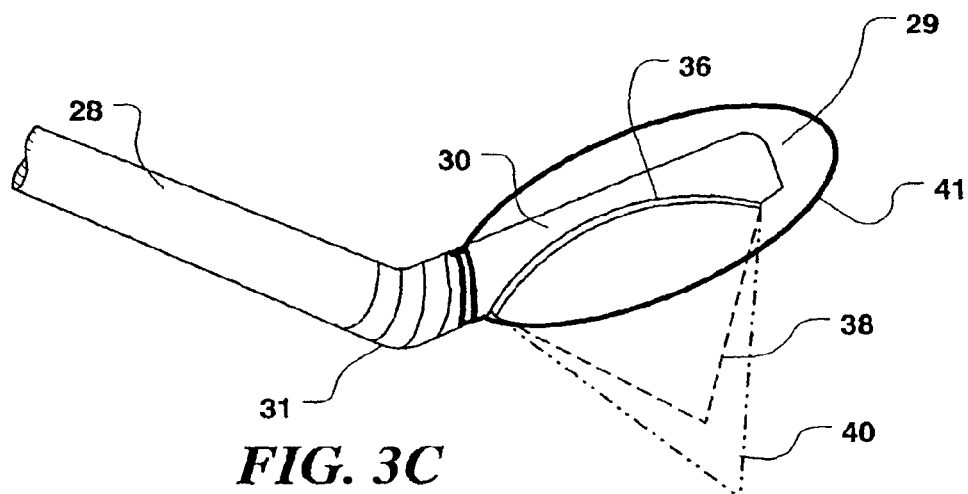
Figure 4A:
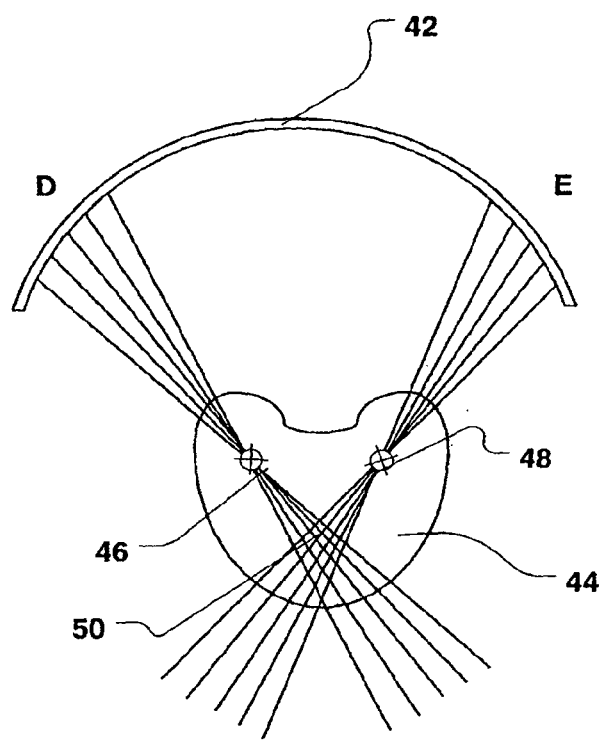
FIGS. 4A and 4B are schematic diagrams of different treatment beam forming techniques used to control the lesion geometry and illustrating spatial lesion formation.
Figure 4B:
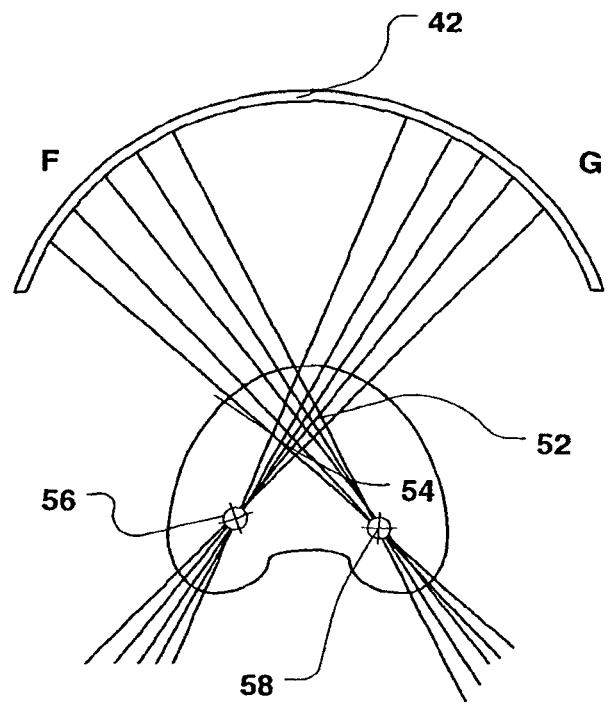
Figure 5A:
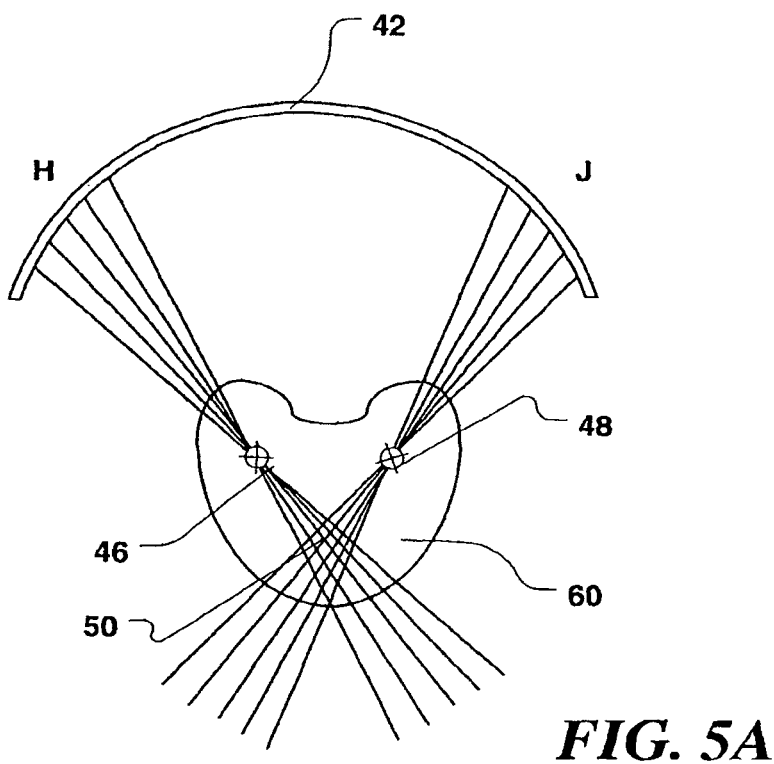
FIGS. 5A and 5B are schematic diagrams of different treatment beam forming techniques used to control the lesion geometry and illustrating spatial-temporal lesion formation.
Figure 5B:
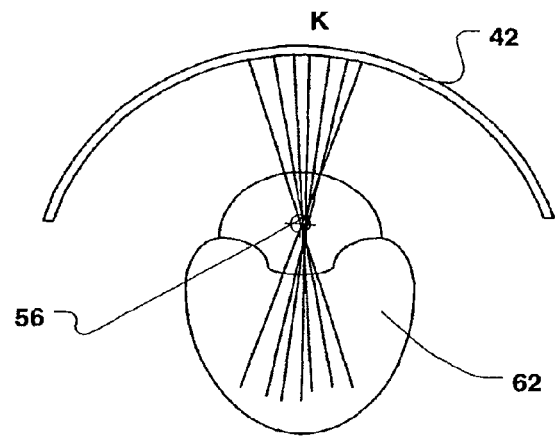

Trans-abdominal ultrasound device 29 shown in FIGS. 3A and 3B has a long shaft 28 that can be inserted into the patient's abdominal cavity through laparoscopic surgery cannula 34, which is disposed in a puncture hole on the abdominal wall. Under visual guidance of a laparoscope, distal end 30 of the device is brought in close contact with the uterine fibroid. As in the trans-cervical device, ultrasound array transducer 36 is preferably mounted at distal end 30 of the device for imaging and therapy. Guided by the ultrasound image, the physician uses the device to necrose the fibroid tissue. The distal end of the device is preferably articulated at a flexible shaft segment 31, as shown in FIG. 3C, with one or two knobs 32 (depending upon whether one or two axes of articulation are provided) that are disposed on handle 33 of the device. This flexible shaft segment permits treatment zone 38 to point in different directions to accommodate different tumor positions. The ultrasound transducer may be disposed in a cover case balloon 41 or other cover at the tip of the device (FIG. 3C).

Cover case balloon 41 is elastomeric and conforms to an outer surface of a tumor, providing more efficient acoustical coupling between the transducer and the treatment area; the curvature of the tumor contour will, in general, be different from the curvature of the ultrasound transducer. Moreover, during a conventional laparoscopic procedure, the patient's abdomen is inflated with $CO_2$ gas to create a large working space. A gas gap between the transducer and the tumor, however, would block the ultrasound transmission. Instead of penetrating into the tumor, the ultrasound beam would be reflected back to the transducer. The therapeutic effect would thus be diminished and the transducer might be damaged by the reflected ultrasound energy.

It thus is important to maintain good acoustic coupling between the treatment tissue and the ultrasound transducer while provide the ultrasound therapy. Water, saline, and most water-based solutions and gels are excellent coupling media. In diagnostic ultrasound imaging, water-based coupling gel is widely used. However, gel may have limitations in trans-abdominal ultrasound therapy for treating uterine fibroids.

Unlike skin, the fibroid is much less compressible. It is also more difficult to apply manual pressure during a laparoscopic procedure to conform the fibroid to the surface contour of the transducer. Gel may be used to fill the remaining gaps, but gas bubbles trapped in the gel are difficult to squeeze out.

In this preferred embodiment of the present invention, water-filled cover case balloon 41 (FIG. 3C) is fabricated of thin elastic material and is placed between the transducer and the fibroid to ensure effective coupling of the ultrasonic energy into the tumor mass. Under a small manual pressure, the balloon is conformed to both the transducer surface and the fibroid surface. If the transducer is inside the balloon, only the fibroid surface needs to be wetted with sterile saline to keep a good coupling to the balloon surface. Alternatively, cover case balloon 41 may be fabricated of a semi-permeable membrane material that enables liquid to weep from inside the balloon. The "weeping" of the fluid from the balloon thus can keep the fibroid surface wet during the treatment. When the internal pressure is higher than the pressure in the abdominal cavity, the sterile saline or water inside the semi-permeable balloon readily weeps through the semi-permeable membrane to create a fluid interface-layer that maintains continuous effective coupling.

Figure 11:
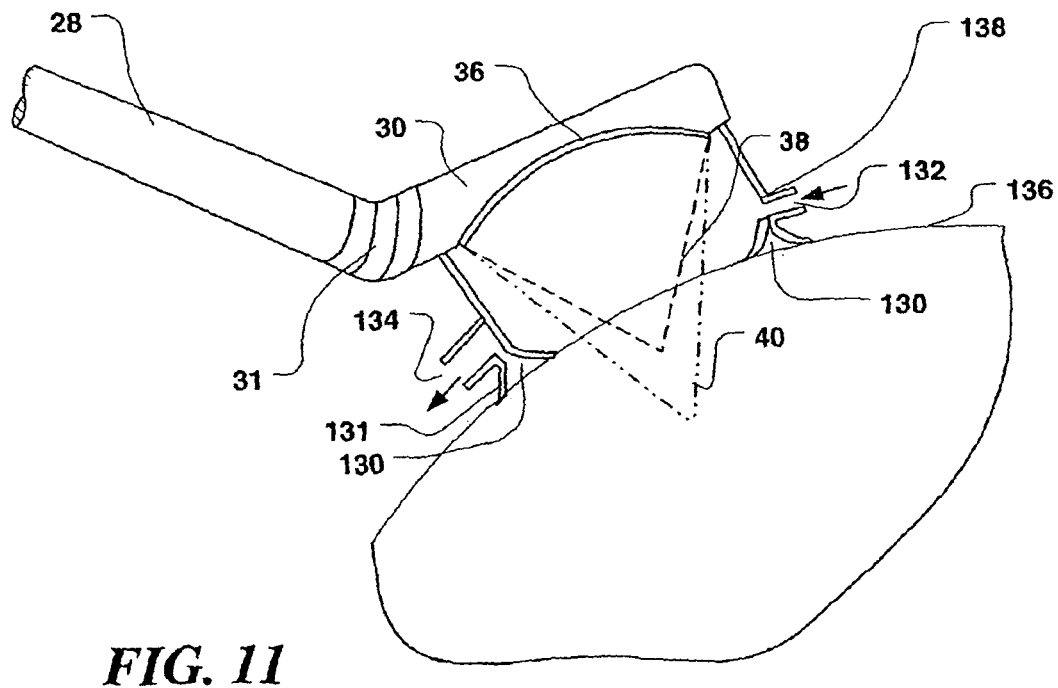
FIG. 11 is a side elevational view of the ultrasound device and a cross-sectional view of a liquid-filled vacuum cap that provides coupling between the fibroid tumor and the ultrasound transducer.

Alternatively, as shown in FIG. 11, a vacuum cap 138 made of soft rubber, plastic, or other elastomeric material, may also be applied at the distal end of the device to provide the acoustic coupling as shown in cross section at FIG. 11. The cap surrounds ultrasound transducer array 36 and is open at its front, opposite the array. The front opening of the cap is large enough to permit the ultrasound beam to pass without obstruction. Around the open end of the cap, a rim 131 has a double lip 130. The double lip is soft and elastomeric and can conform to the shape of a tumor surface 136. A vacuum port 134 is provided in fluid communication with the double lip, and a vacuum source coupled to this port provides a negative pressure within the double lip that holds the cap tightly on the tumor. Sterile water is then provided through a port 132 that communicates with an interior of the cap to provide the acoustic coupling between the transducer and the tumor. The cap works as a wall to block gas from getting into the cap. In case there are any minor leaks, the leaking gas and water are removed immediately at the double lip.

To protect the ultrasound transducer against accidental damage caused by the reflected ultrasound power when there are large gas bubbles or gaps between the transducer and the tumor, or when the device is lifted from the tumor while the high intensity ultrasound output is still on, the present invention preferably uses the ultrasound imaging capability to detect the existence of gas. When a gas gap exists, it causes a strong reflection detected when ultrasound imaging. The reflection may also bounce back and forth between the transducer and the gas gap, resulting in a reverberation (multiple reflections). The strong reflection or reverberation appear(s) as very bright echoes in a large portion of the image. When observing this unique echo image, the medical practitioner may adjust the position or the coupling of the ultrasound device to eliminate the trapped gas. As an alternative, an automatic gas detection technique may be used to avoid the reflection damage. By using the unique characteristics of the gas in the reflected echo signal, the system may detect its existence during the imaging process. When the strong echo is detected, the system may automatically turn off the high intensity ultrasound output to the area where there are gas gaps. This automatic power shut down process is accomplished almost instantaneously, so that thermal damage to the transducer array is avoided.

During therapy application, the ultrasound transducer generate heat internally. This heat can possibly cause damage or reduce the service life of the transducer array. Moreover, if the transducer array touches the tumor tissue directly, the high temperature of the transducer array can prematurely, or inadvertently, necrose the tissue surface. The high acoustic absorption of the necrosed tissue at the surface would also prevent the ultrasound beam from penetrating deep into the tumor, so that the deep tumor tissue might not be properly treated. It is therefore very important to keep the temperature of the transducer array and at the tissue interface relatively low during the treatment.

Figure 13:
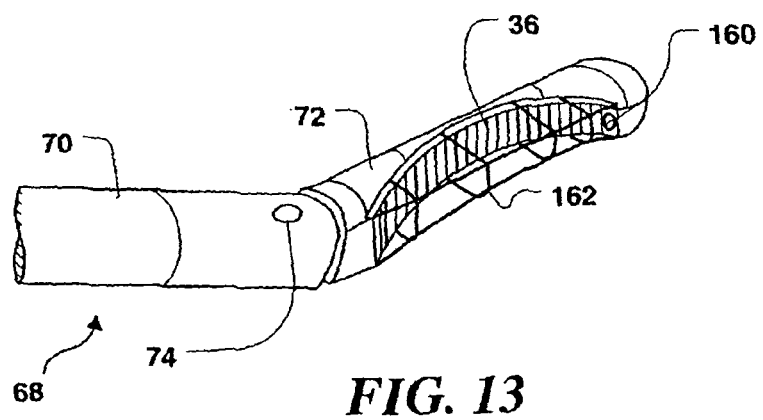
FIG. 13 is an isometric view of a portion of an ultrasound device that includes a structure to maintain a gap between the tissue being treated and an ultrasound transducer array, to convey a coolant liquid.

A plurality of techniques can be employed to cool the transducer array. The simplest approach is to immerse the transducer in water, maintain a gap between the transducer surface and the tumor, and then ensure that the water flows through the gap during the treatment. Two water channels preferably disposed inside the device casing to circulate the cooling fluid may optionally be used for this purpose. The ultrasound transducer array is disposed in one of the channels. Alternatively, both the transducer and the tumor may be immersed in water. In the trans-cervical approach, the uterine cavity is conveniently filled with water. In certain trans-abdominal situations, it may be possible to fill a portion of the abdominal cavity with water. And, in some non-invasive situations it is possible to construct a water dam, sealed at its periphery to the organ surface, creating a water pool in which the applicator may be positioned. As shown in FIG. 13, a thin-wire fence 162 or frame attached to distal end 72 maintains a gap between transducer array 36 and the first interface of patient tissue (e.g., the tumor's outside surface). A variety of such useful standoff structures may be employed, as best suited for the geometric requirements of the application and specific applicator designs. During treatment, a water jet from a port 160 introduces water, or saline, into the gap. Circulation of conditioned water through one or more such ports may be used to control water temperature, pressure, chemical composition, gas content, or volume. Alternatively, the transducer array may be cooled by using a thermal-conductive, acoustic-matching layer (e.g., aluminum) bonded to the piezoelectric ceramic of the ultrasound transducer array. This thermal-conductive layer removes the heat from the transducer ceramic. The heat is removed by water flowing in attached lines or by heat sinks that are connected to the thermal-conductive layer.

To simplify the device design and to reduce the size of the endoscopic instrument, one ultrasound transducer array is used for both imaging and therapy. A concave transducer array provides a good compromise to simplify the design for both functions. Natural focusing of the concave geometry simplifies the ultrasound beam forming, where there is no (or less) phase delay needed, and cross-talk among array elements is less of a problem. Because of the minimum phase delay required, larger element pitch size can be used. Large pitch size reduces the number of elements in the array and the number of electronic signal channels required. It also helps to reduce the cost of the transducer and the cost of the control unit. Treatment area 38 is geometrically inside imaging area 40 of the array (see FIG. 3B). The entire treatment area is under the ultrasound imaging monitoring—there is no blind spot in the treatment area.

Figure 12:
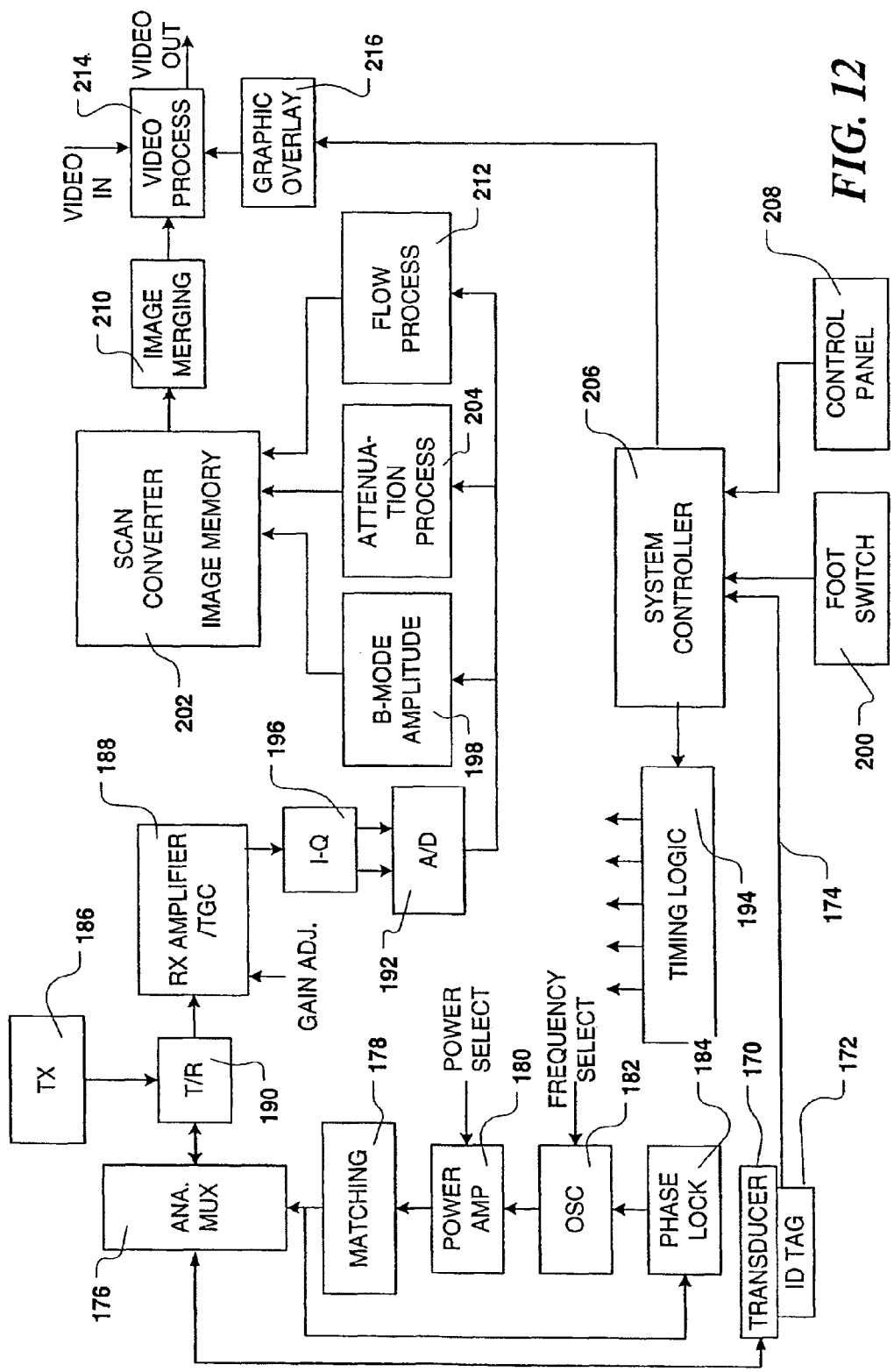
FIG. 12 is a system block diagram of the control electronics in the control unit.

FIG. 12 is a simplified block diagram of the electronic control system according to the invention. The specific applicator device connected to the control system is recognized electronically by a system controller 206, which reads applicator data from a memory device, an ID tag 172. Such data include specific functional and calibration information. A switch matrix 176 connects a concave transducer array 170 to the therapeutic circuitry or to the imaging circuitry. During imaging, an imaging transmitter 186 generates pulse sequences to drive the ultrasound transducer array through a transmit-receive switching matrix 190. The imaging receiver amplifies and processes the echo signals captured by the transducer array. During the therapy phase, switch matrix 176 connects the transducer array to the therapeutic transmitter chain to form and steer a high intensity ultrasound beam within the tissue being treated. To monitor the treatment process, the transducer array may be periodically switch back to the imaging circuitry to form frames of ultrasound images during the treatment.

System controller 206 provides overall control and synchronization of the multiplicity of functions executed by the system including an operator interface control panel 208, a foot switch 200 that is used for initiating and arresting therapy, and a timing logic 194, employed for establishing appropriate phasing of the therapeutic phased array transmit chain. This chain comprises a primary oscillator 182, a phase locked loop 184, a multi-channel power amplifier 180 and matching networks 178. Additionally, timing logic 194 provides data to the imaging chain that includes the receive amplifiers and time-gain compensation circuits 188, a quadrature detection circuit 196, an analog-to-digital conversion circuit 192, an Intensity (B) mode processing circuit 198, an attenuation processing circuit 204, a Doppler flow processing circuit 212, and a scan conversion circuit 202. Images of the target tissue are converted to a format compatible with standardized operating room video display in image merging circuits 210 and mixed with other video sources (e.g., hysteroscopic optical imaging), and user interface graphics, and processed in graphic overlay 216, which is included in a video processor module 214, for display.

Thermally necrosed tissue has a much higher acoustic attenuation (>1.0 dB/cm/MHz) than the untreated tissue (0.4-0.7 dB/cm/MHz). This property may be used to monitor or visualize the treatment area. One technique to measure the tissue attenuation change is to measure the frequency spectral change in the echo signal. High frequency components in the frequency band are attenuated more than the low frequency components. By subtracting the spectrum before the treatment from the spectrum after the treatment, the attenuation change can be measured. If the subtracted spectrum is near zero, it indicates that the tissue where the echo is acquired has not been treated. If the result of spectrum subtraction has a significant slope, it means the tissue attenuation has changed, indicating that this area has been necrosed.

Alternatively, or in combination with this attenuation imaging, elasticity imaging may be employed to assess tissue state before, during, or after ultrasonic treatment. Elasticity imaging, the principles of which are well known in the art, provides a visualization of physical and mechanical tissue properties. Necrosed tissues are stiffer and demonstrate elasticity changes. Treatment endpoints may be manually or automatically controlled (under operator control) by use of elasticity imaging parameters.

As an alternative method of therapy that may reduce the treatment time even further, the patient may be given an injection of ultrasound contrast agent, which is a solution of encapsulated air-containing micro-bubbles that are sufficiently small to circulate safely in the blood and blood vessels. When the bubbles are flowing through the fibroid, they will be hit by the high intensity therapeutic ultrasound. The bubbles enhance the ultrasound heating process at the treatment area and make the treatment more efficient.

As a further alternative method of therapy, cavitation may be utilized as a mechanism for speeding effective treatment. Ultrasound with high acoustic pressure and lower frequency increases the likelihood of stimulating the onset of cavitation. The presence of contrast media or bubbles also encourages cavitation. Cavitation can aggressively disrupt tissue and increase energy transfer for an enhanced heating effect.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An ultrasonic system for destroying undesired tissue at an internal site within a body of a patient, comprising:
   (a) a probe that is sized to be inserted within a body of a patient;
   (b) an ultrasonic transducer mounted proximate a distal end of the probe, said ultrasonic transducer being adapted to couple to a power supply to selectively energize the ultrasonic transducer so that it produces a focused beam of high intensity ultrasonic energy configured to heat tissue between the transducer and a focal point based on a combination of at least two of an f-number, an intensity, a time, and a direction of the beam of high intensity ultrasonic energy and to treat the undesired tissue at the focal point, wherein said high intensity ultrasonic energy is configured to heat tissue between the transducer and focal point to a level sufficient to cause a lesion to form between the focal point and the ultrasonic transducer and to not cause a lesion to form substantially beyond the focal point; and
   (c) an ultrasound transmissive interface that is coupled to the distal end of the probe, said ultrasound transmissive interface being disposed and adapted to transmit the high intensity ultrasonic energy produced by the ultrasonic transducer into a target, said high intensity ultrasonic energy increasing a temperature of the undesired tissue.

2. The ultrasonic system of claim 1, wherein the ultrasound transmissive interface comprises an elastomeric cavity that is adapted to contain a liquid, said elastomeric cavity being disposed between the ultrasonic transducer and a surface of a contacted tissue so that the high intensity ultrasonic energy passes through the liquid within the elastomeric cavity and into the contacted tissue.

3. The ultrasonic system of claim 2, wherein the elastomeric cavity is formed at least in part from a semi-permeable membrane, so that the liquid from within the elastomeric cavity weeps onto a surface of the contacted tissue to increase an efficiency for coupling the high intensity ultrasonic energy into the contacted tissue.

4. The ultrasonic system of claim 2, wherein the ultrasound transmissive interface comprises a cap made of an elastomeric material and disposed to surround the ultrasonic transducer, said cap being adapted to seal against the contacted tissue and to contain a liquid that increases an efficiency with which the high intensity ultrasonic energy is coupled into the contacted tissue.

5. The ultrasonic system of claim 4, wherein the cap includes a rim having a double lip formed around a perimeter and includes a passage adapted to couple to a vacuum line so that the rim of the cap is held against a surface of the contacted tissue, sealing the liquid inside of the cap.

6. The ultrasonic system of claim 1, wherein said high intensity ultrasonic energy is configured to heat tissue between the transducer and focal point to a temperature of 50° C. or more.

7. The ultrasonic system of claim 1, wherein the lesion has a volume of about 4.5 cubic centimeters.

8. A method for administering an ultrasonic therapy to a target, comprising the steps of:
   (a) providing an ultrasonic transducer that emits a focused high energy ultrasonic energy when energized;
   (b) positioning the ultrasonic transducer to focus it at an imaged target;
   (c) directing the ultrasonic transducer toward a desired focal point within the target;
   (d) energizing the ultrasonic transducer so that it emits the focused high energy ultrasonic energy at the desired focal point, causing heating of a portion of the target disposed at the desired focal point; and
   (e) controlling a combination of at least two of an f-number, an intensity, a time, and a direction of the high intensity ultrasonic energy emitted into the target without moving the focal point to cause an initial lesion to grow toward the ultrasonic transducer and in at least one other dimension and not away from the ultrasonic transducer.

9. The method of claim 8, wherein a desired shape and size of the lesion are selected so that formation of the lesion substantially deprives the target of a blood supply, causing the ultimate destruction of the target.

10. The method of claim 8, wherein a desired shape and size of the lesion are selected to cause heating of a blood vessel.

11. The method of claim 8, wherein the target is a blood vessel.

12. The method of claim 8, further comprising imaging the target.

* * * * *